US008158944B2

(12) United States Patent
Tolton et al.

(10) Patent No.: US 8,158,944 B2
(45) Date of Patent: Apr. 17, 2012

(54) ATMOSPHERIC GAS DETECTION APPARATUS AND METHOD

(75) Inventors: Boyd T. Tolton, Edmonton (CA);
Adrian Banica, Edmonton (CA);
Douglas W. Miller, Saskatoon (CA);
Bogdan Teianu, Edmonton (CA)

(73) Assignee: Synodon Inc., Edmonton (CA)

( * ) Notice: Subject to any disclaimer, the term of this patent is extended or adjusted under 35 U.S.C. 154(b) by 0 days.

(21) Appl. No.: 12/552,248

(22) Filed: Sep. 1, 2009

(65) Prior Publication Data
US 2010/0102232 A1    Apr. 29, 2010

Related U.S. Application Data

(63) Continuation of application No. PCT/CA2008/000396, filed on Mar. 3, 2008.

(60) Provisional application No. 60/892,821, filed on Mar. 2, 2007.

(51) Int. Cl.
*G01N 21/35*    (2006.01)
(52) U.S. Cl. ..................................... 250/338.5
(58) Field of Classification Search ............... 250/338.5, 250/253
See application file for complete search history.

(56) References Cited

U.S. PATENT DOCUMENTS

| | | | | |
|---|---|---|---|---|
| 4,520,265 A | * | 5/1985 | Griggs et al. | 250/338.5 |
| 4,963,742 A | * | 10/1990 | Abernathy | 250/338.5 |
| 5,471,056 A | * | 11/1995 | Prelat | 250/253 |
| 2004/0232338 A1 | * | 11/2004 | Tolton et al. | 250/338.5 |
| 2005/0105103 A1 | * | 5/2005 | Schietinger et al. | 356/630 |
| 2005/0151965 A1 | | 7/2005 | Bissett, III | |
| 2006/0005077 A1 | * | 1/2006 | Miller | 714/33 |

FOREIGN PATENT DOCUMENTS
EP    1 564 544 A1    8/2005

OTHER PUBLICATIONS

Tolton, B.T., and D. Yashcov, "A Concept for a Gas-Filter Correlation Radiometer to Remotely Sense the Atmospheric Carbon Dioxide Column From Space," IEEE International Geoscience and Remote Sensing Symposium [IGARSS '02], Toronto, Jun. 24-28, 2002, vol. 4, pp. 2118-2120.

Ho, S.-P., et al., "Improvement of the Global Surface Emissivity From MOPITT Measurements and Its Impacts on the Retrievals of Tropospheric Carbon Monoxide Profiles," in S.C.Tsay, et al. (eds.), Proceedings of SPIE—Passive Optical Remote Sensing of the Atmosphere and Clouds IV 5652(1):124-135, 2004.

(Continued)

*Primary Examiner* — Constantine Hannaher
(74) *Attorney, Agent, or Firm* — Christensen O'Connor Johnson Kindness PLLC

(57) ABSTRACT

A method of detecting a target gas includes the step of traversing a target area with a gas-filter correlation radiometer having a field of view oriented towards the target area. The gas-filter correlation radiometer receives reflected radiation in a passband from the target area and produces gas-filter correlation radiometer signals from the received reflected radiation. A surface reflectivity spectral profile of the target area is determined. The presence of the target gas in the target area is then determined based upon the received reflected radiation and the surface reflectivity spectral profile of the target area.

26 Claims, 16 Drawing Sheets

Simultaneous FOVs

OTHER PUBLICATIONS

Hunt, L.A., and N. A. Ritchey, "Simultaneous Earth Views From CERES, MISR and MOPITT," Proceedings of IEEE International Geoscience and Remote Sensing Symposium (IGARSS '04), Anchorage, Alaska, Sep. 20-24, 2004, vol. 7, pp. 4523-4526.

Pfister, G., et al., "Effects of a Spectral Surface on Measurements of Backscattered Solar Radiation: Application to the MOPITT Methane Retrieval," Journal of Atmospheric and Oceanic Technology 22(5):566-574, May 2005.

Supplementary European Search Report mailed Nov. 17, 2011, issued in corresponding European Application No. EP 08 714 716, filed Mar. 3, 2008, 12 pages.

Yamaguchi, Y., et al., "Overview of Advanced Spaceborne Thermal Emission and Reflection Radiometer (ASTER)," IEEE Transactions on Geoscience and Remote Sensing 36(4):1062-1071, Jul. 1998.

Xiong, X., and W. Barnes, "An Overview of MODIS Radiometric Calibration and Characterization," Advances in Atmospheric Sciences 23(1):69-79, Jan. 2006.

* cited by examiner

ATMOSPHERIC GAS DETECTION APPARATUS AND METHOD

TECHNICAL FIELD

Apparatus and methods for gas detection.

BACKGROUND

Infrared remote sensing of trace gases in the lower atmosphere from a satellite or aircraft platform is an extremely difficult task because the instrument must view the surface of the Earth. To maximise the energy gathered and to minimise noise due to scattering losses and clouds in the atmosphere, a nadir (or near-nadir) viewing geometry is required. Also, since the trace gas near the surface and the ground are approximately the same temperature, there is very little radiative contrast between the thermal emission of the gas and the surface at wavelengths longer than 3.5 µm. As a result, measurements must, in this embodiment, be made at shorter wavelengths, where reflected solar radiation becomes a significant component in the upwelling radiance. Consequently, any short-scale spatial or temporal variations in the surface, the atmosphere and/or the environment add noise into the measurement as the instrument passes over the surface.

The primary complications in such remote sensing measurements are spatial and temporal variations in the surface, the atmosphere and the environment. Any variations as the instrument passes over the surface has the potential to add noise and/or error to the measurement. The main sources of spatial and temporal variations include, variations in {a} surface reflectivity and emissivity, {b} surface temperature, {c} angle of the surface (relative to the nadir), {d} solar zenith angle (SZA, the angle between the Sun and the vertical), {e} scattering properties of the surface, and {f} absorption from gases in the atmosphere. The following section discusses each of these sources of error.

Reflectivity and emissivity—Reflectivity and emissivity are related by Kirchoff's Law, which states that the emissivity ($\epsilon_\lambda$) of a surface equals absorptivity ($A_\lambda$), and equals one minus the reflectivity ($R_\lambda$).

Kirchoff's law: $\epsilon_\lambda = A_\lambda = 1 - R_\lambda$

FIG. 1A through 1E shows the total hemispheric reflectivity of many natural and man-made surfaces in the infrared (2-4 µm, 2500-5000 cm$^{-1}$), obtained from the Jet Propulsion Laboratory, NASA, Aster Spectral Library. FIG. 1A shows the reflectivity of vegetation, FIG. 1B shows the reflectivity of certain types of rocks, FIG. 1C shows the reflectivity of certain types of soils, FIG. 1D shows the reflectivity of certain man-made materials, and FIG. 1E shows the reflectivity of snow, ice and water. These figures show large variations in the infrared reflectivity for all materials and between different materials. As a result, the upwelling radiance from the surface is strongly affected by the spatial distribution of surface types in any remote sensing instrument's field-of-view (FOV).

The emission of the surface and gases in atmosphere—The emission of the surface and gases in atmosphere are a function of their temperatures and their emissivities. In the infrared, most surfaces have a significant emissivity. Also, the higher the temperature, the larger the emission from the surface and atmosphere. In general, this is only a significant issue at wavelengths >3 µm, when thermal emission from the surface and atmosphere become a significant component in the background radiation field.

Reflected solar energy—The amount of solar energy reflected from a surface is dependent on the flux of solar energy incident on the surface. As the SZA increases, the incident energy per unit area (which is reflected) decreases, due to geometry and absorption by the atmosphere. This is also effected by the angle of the surface (ie. the topography) relative to the Sun.

Scattering properties of a surface—The scattering (reflective) properties of the surface greatly affect the upwelling reflected solar radiance. Energy which is scattered from the surface may be reflected in all directions. Some surfaces, such as oceans, are highly specular (minor-like) reflectors. Other surfaces, such as vegetation, are highly lambertian (isotropic) reflectors. In general, most surfaces are somewhere between specular and lambertian. FIG. 2A through 2D shows various types of reflectors from an ideal specular reflector in FIG. 2A to an ideal lambertian reflector in FIG. 2D. As a consequence, upwelling radiance varies with the scattering properties of the surface materials.

Distribution of concentration of gases—The spatial and temporal distribution of the concentration of gases that absorb energy within the passband of the remote sensing measurement may vary spatially, resulting in variations in upwelling radiance.

The upwelling radiance from the Earth's surface varies spatially, temporally and spectrally. In general these variations occur over all spatial scales in which the atmosphere is remotely sensed. Any remote sensing technique that observes the surface will require a methodology to remove or reduce the noise induced by these variations.

Gas-Filter Correlation Radiometry

One remote sensing technique that has been utilized for remote sensing of trace gases near the surface is known as Gas-Filter Correlation Radiometry (GFCR). A GFCR is a remote sensing radiometer that uses a sample of the gas as a spectral filter, providing enhanced sensitivity and selectivity to that gas. FIG. 3 is a schematic showing the principles of GFCR. Incoming radiation 12 is passed through a gas cell 14, known as a correlation cell, which is undergoing a gas-density modulation (molecules per cm$^2$) along its optical path (the gas in the correlation cell is the same as the gas being remotely sensed). The radiation is then passed through a narrow bandpass filter 16, which passes only a narrow spectral range selected to cover an absorption band of the gas of interest. The radiation is then measured by an infrared detector 18. In other embodiments, the type of detector will depend on the radiation being detected. The modulation of the gas-density in the correlation cell produces a modulation in detector signal, which is measured using a phase-sensitive detector 20. This signal corresponds to the energy entering the radiometer at wavelengths corresponding to the absorption lines in the passband of the gas of interest.

In operation, gas density modulation has been performed by a number of techniques. A Selective Chopper radiometer (SCR) modulates gas-density by "chopping" between two correlation cells of different gas pressure, and sometimes length. A Pressure-Modulator Radiometer (PMR) modulates the pressure of the gas inside a static correlation cell. A Length Modulated Radiometer (LMR) modulates the path length of gas inside the correlation cell by rotating a bow-tie shaped rotor of an inert optical material inside the cell. The most recent satellite instrument to attempt to measure lower atmospheric trace gases using GFCRs was the MOPITT (Measurements Of Pollution In The Troposphere) instrument launched on NASA's Terra satellite in December 1999.

FIG. 4 is a schematic diagram detailing a recent fourth configuration of a GFCR, known as a Simultaneous-View Correlation Radiometer (SVCR). In this configuration, the incoming energy is split by a beam splitter 22 onto two optical paths 24 and 26 with two gas cells 28 and 30 of different gas density, and two infrared detectors 32 and 34. Gas cell 28 may be evacuated. It may also be filled with an optically inert gas. Gas cell 30 may be referred to as a correlation cell. Instead of a sequential gas-density modulation in detector signals, the GFCR measurement is performed by comparing the simultaneous signals of the two detectors using a computer 36.

FIG. 5 illustrates how a GFCR 38 detects the presence of the trace gas in its FOV. The two channels 44 and 46 of the radiometer detect two signals, $S_1$ and $S_2$ respectively. If a cloud of absorbing gas 40 (the same gas as in the correlation cell 30) is in the FOV 42 of the GFCR 38, the signal in the first channel 44 is reduced due to the absorption of this gas ($S_1-\epsilon$). However, since the second channel 46 already has the energy absorbed by the gas in the correlation cell 30 (at the wavelengths corresponding to the absorption lines of the gas), the signal does not change (at least to first order).

In operation, two GFCR signals are defined, a difference signal ($S_{diff}$) and an average signal ($S_{avg}$). $S_{diff}$ is the difference between $S_1$ and $S_2$, and $S_{avg}$ is the average of $S_1$ and $S_2$. $S_{diff}$ is primarily a measurement of the upwelling radiance at the wavelengths corresponding to the absorption lines of the gas of interest. $S_{avg}$ is primarily a measure of the upwelling radiance across the entire passband. A third GFCR signal, known as the "instrument signal", is often also defined, the "difference-to-average ratio" ($S_{diff}/S_{avg}$). Defining the instrument signal in this matter is convenient as the value is unitless, and the effects of any "grey" absorption or scattering features (ie. constant or uniform over the radiometer passband) in the atmosphere, environment or the instrument are removed. This includes any uniform variation in the surface reflectivity.

For GFCR measurements of the lower atmosphere, $S_{diff}/S_{avg}$ is commonly used because it greatly reduces the effects of the generally unknown and highly variable surface reflectivity. This strategy does greatly reduce the errors induced by variations in the upwelling source radiance. However, the short wavelength "solar" channels of MOPITT which were to measure the total CO (2.34 μm) and $CH_4$ (2.26 μm) column concentrations were noisy and did not achieve their designed accuracy. These channels worked best over the oceans, where the spatial surface variations were minimal.

Surface Reflectivity

Until recently, it has been assumed that the primary cause for the failure of the MOPITT solar channels was that the LMRs used in these channels made sequential measurements of the gas density states. The rotors in the MOPITT LMRs modulated the gas path length at a rate of 40 Hz. In the time for the LMR to go from one gas-density state to the other, the FOV of the instrument (nominally 20×20 km) moved approximately 175 m across the surface. As such, any spatial variations in the upwelling radiance was convolved into instrument signals, creating noise. This effect was confirmed by observing large peaks in measurement noise when the FOV of MOPITT passed over a major transition in surfaces, such as from land (high reflectivity) to the ocean (low reflectivity). This issue can be relieved by changing the type of GFCR used, from the LMR to a form which makes simultaneous measurements of the two gas-density states (such as the SVCR).

However, a second problem relating to surface variations has recently been identified for surface-viewing remote sensing GFCR measurements. As stated previously, by defining the instrument signal as the ratio of the difference-to-average signals ($S_{diff}/S_{avg}$), any "grey" or uniform variation (over the passband) in the surface reflectivity/emissivity is removed. However, it is rarely the case that variations in the reflectivity over the passband are uniform. Instead, as the GFCR moves over different surface types, the upwelling radiance from different sections of the instrument passband varies. This results in a change in the "weighting" of different sections of the passband in the GFCR signals. Since the absorption lines of the gas of interest are neither uniformly nor randomly distributed over the passband (either in strength or in position), the instrument signal ($S_{diff}/S_{avg}$) varies with the surface type. For example, if a change in the surface reflectance increases upwelling radiation in a region of strong absorption of the measured gas, this will result in an increase $S_{diff}$ but have a smaller relative increase on $S_{avg}$. Similarly, if a change in the surface reflectance increases upwelling radiation in a region of weak(er) absorption by the measured gas, this will result in an increase $S_{avg}$ but have a much smaller relative increase on $S_{diff}$. Consequently, variations in the reflectivity of the surface over the passband add noise/error into the GFCR instrument signal ($S_{diff}/S_{avg}$).

As an example, FIGS. 6 and 7 show the passband of one of the MOPITT solar CO (channel #2) and $CH_4$ (channel #4) channels, including the bandpass filter transmission profiles of the channels, the transmission of the long path density state of the correlation cell of the LMR, and the measured total hemispheric reflectance of dry grass, conifer needles and water. As can be seen the distribution of $CH_4$ and CO absorption lines within the passbands are neither random nor uniform. For the $CH_4$ case, stronger absorption occurs on the lower wavenumber (higher wavelength) side of the passband. If the surface reflectivity change uniformly over the passband (ie. a "grey" or uniform variation), then the net effect on the $S_{diff}/S_{avg}$ signal will be zero (ie. the $S_{diff}$ and $S_{avg}$ signals change by the same fractional amount). However, if the surface reflectivity changes by different amounts over the passband (as highlighted by the differences in the three reflectivity curves), this will cause an offset (ie. error) in the $S_{diff}/S_{avg}$ signal.

To further highlight the potential impact of this surface reflectance effect, FIG. 8 shows the passband of the RealSens™ GFCR instrument for detection of ethane ($C_2H_6$), plus the total hemispheric reflectance curves for seven different surface types. RealSens™ is a recent commercial aircraft-based GFCR instrument for remotely sensing the presence of leaked natural gas. This figure shows that for the RealSens™ measurement, surface reflectivity is an important factor in data retrieval, more so than for the MOPITT solar channels (although it is still an important and limiting problem for the MOPITT GFCRs).

It should be noted, of all the sources of variance in upwelling radiation listed above, only reflectivity (and associated emissivity) and absorption by gases in the atmosphere produce non-uniform variations over the passband in the upwelling radiation. All other factors, including SZA, surface angle, and scattering induce, to first order, introduce only uniform variations (over the passband) in the upwelling radiation. Therefore, surface reflectivity is a primary source of short spatial scale noise in nadir-viewing GFCR measurements.

SUMMARY

There is provided a method of detecting a target gas. The method comprises the step of traversing a target area with a gas-filter correlation radiometer having a field of view oriented towards the target area. The gas-filter correlation radiometer receives reflected radiation in a passband from the target area and produces gas-filter correlation radiometer signals from the received reflected radiation. A surface reflectivity spectral profile of the target area is determined. The presence of the target gas in the target area is determined based upon the received reflected radiation and the surface reflectivity spectral profile of the target area. Determining the presence of the target gas may comprise comparing the gas-filter correlation radiometer signals with hypothetical gas-filter correlation radiometer signals. Hypothetical gas-filter correlation radiometer signals may be generated by using an atmospheric radiative transfer model. Determining the presence of the target gas may comprise determining a concentration of the target gas.

According to an embodiment, determining the surface reflectivity spectral profile may comprise obtaining multi-spectral measurements in at least the passband from the field of view of the gas-filter correlation radiometer, and in an embodiment may comprise relating the multi-spectral measurements to signals generated by an atmospheric radiative transfer model, and may comprise relating the multi-spectral measurements to a calibrated multi-spectral measurement or modifying a calibrated multi-spectral measurement using the signals generated by the atmospheric radiative transfer model. The atmospheric radiative transfer model may be based on variables comprising one or more of atmospheric temperature, atmospheric pressure, atmospheric humidity, radiatively active gas concentration profiles, surface temperature, solar radiance, solar zenith angle, surface topography, gas-filter correlation radiometer variables and characteristics, other detection equipment variables and characteristics, estimated surface reflectivity spectral profile curves, and gas concentration measurements. Determining the surface reflectivity spectral profile of the target area may comprise removing effects of thermal emission in the reflected radiation received from the target area. Removing effects of thermal emission may comprise subtracting thermal emission effects from the multi-spectral measurements and the signals generated by the atmospheric radiative transfer model.

According to an embodiment, determining the presence of the target gas comprises comparing the gas-filter correlation radiometer signals with hypothetical gas-filter correlation radiometer signals, and may further comprise generating the hypothetical gas-filter correlation radiometer signals by using an atmospheric radiative transfer model.

According to an embodiment, the gas-filter correlation radiometer signals and the multi-spectral measurements may be respectively obtained using the gas-filter correlation radiometer and a separate spectrometer oriented to receive reflected radiation from the target area simultaneously, or in another embodiment may be obtained by splitting the received reflected radiation into at least two separate paths within the gas-filter correlation radiometer, one of which paths is used to calculate the gas-filter correlation radiometer signals and another of which paths is used to calculate the multi-spectral measurements.

According to an embodiment, there is provided a method of detecting a target gas. The method comprises the step of measuring reflected radiation from the target area using a spectrometer. The surface reflectivity spectral profile of a target area is determined using an atmospheric radiative transfer model and the reflected radiation measured by the spectrometer. Reflected radiation from the target area is measured using a gas-filter correlation radiometer. The presence of a target gas is determined based on the reflected radiation measured by the gas-filter correlation radiometer and the surface reflectivity spectral profile.

There is also provided a detector for detecting gases, comprising a gas-filter correlation radiometer having a first field of view oriented toward a target area. The gas-filter correlation radiometer in operation has as input reflected radiation from the target area and has as radiometer output a first signal corresponding to detection of a target gas between the gas-filter correlation radiometer and the target area. There is provided a spectrometer that has a second field of view oriented toward the target area. The spectrometer in operation has as input reflected radiation from the target area and having as spectrometer output a second signal corresponding to a surface reflectivity spectral profile of the target area. Detector electronics are connected to receive the radiometer output and the spectrometer output. The electronics have in operation as detector output a gas detection signal based on the radiometer output and the spectrometer output. The spectrometer and the gas-filter correlation radiometer may be separate devices. The gas-filter correlation radiometer and the spectrometer may be contained within a single apparatus. The spectrometer may have a spectrometer passband divided into channels, and the gas-filter correlation radiometer may have a radiometer passband such that the channels of the spectrometer at least partially overlap with the radiometer passband. The gas-filter correlation radiometer and the spectrometer may share at least one converter of light to electrical energy. The spectrometer may be an imaging spectrometer. The spectrometer may comprise a detector array having a spatial dimension and a spectral dimension.

These and other aspects of the device and method are set out in the claims, which are incorporated here by reference.

BRIEF DESCRIPTION OF THE FIGURES

Embodiments will now be described with reference to the figures, in which like reference characters denote like elements, by way of example, and in which.

DETAILED DESCRIPTION

Simulated Errors in GFCR Retrievals

To examine the effects of surface variations on GFCR measurements the MOPITT solar channels and the RealSens™ instrument have been modelled. In the following sections, the results of simulations are presented to examine the effects of varying surface reflectance for these instruments.

Simulated Errors in MOPITT Solar Channels Retrievals

The MOPITT solar channels were designed to measure the atmospheric column concentrations (from the surface to the top of the atmosphere) of CO and $CH_4$. The accuracy goal for MOPITT column concentrations was ±10% for CO ($\approx$±10 ppb) and ±1% for $CH_4$ ($\approx$±17 ppb). The CO and $CH_4$ columns were measured using near infrared (short wave, SW) bands of CO and $CH_4$, at 2.34 µm and 2.26 µm, respectively. Neither of the solar CO and $CH_4$ channels on MOPITT have met the design specification for sensitivity.

A series of atmospheric radiative transfer model calculations of the sensitivity of a "MOPITT-like" LMR measuring the CO and $CH_4$ column were performed using the bandpass filter profiles for Channels #2 and #4 of MOPITT. FIG. 9A through 9F show the atmospheric transmission (double-pass through atmosphere) of CO, $CH_4$, $H_2O$, and $N_2O$, along with the transmission profiles for the bandpass-filters (from 4150 to 4600 $cm^{-1}$, or 2.17 to 2.41 µm).

Figure 6:
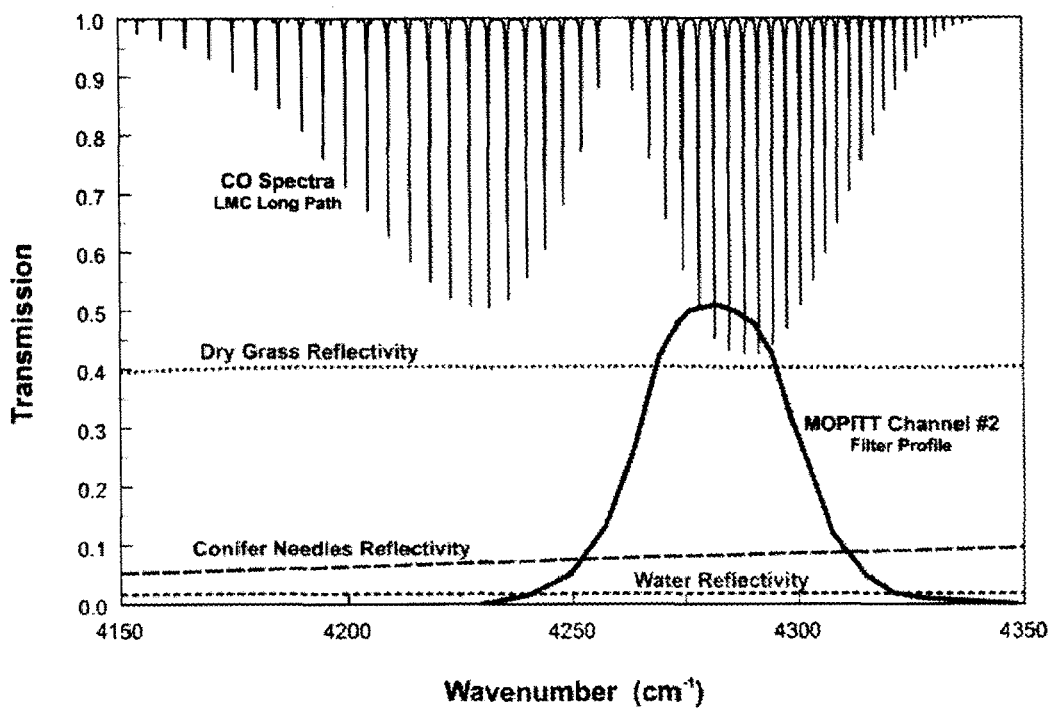
FIG. 6 is a graph of the passband of the MOPITT solar CO channel.
Figure 7:
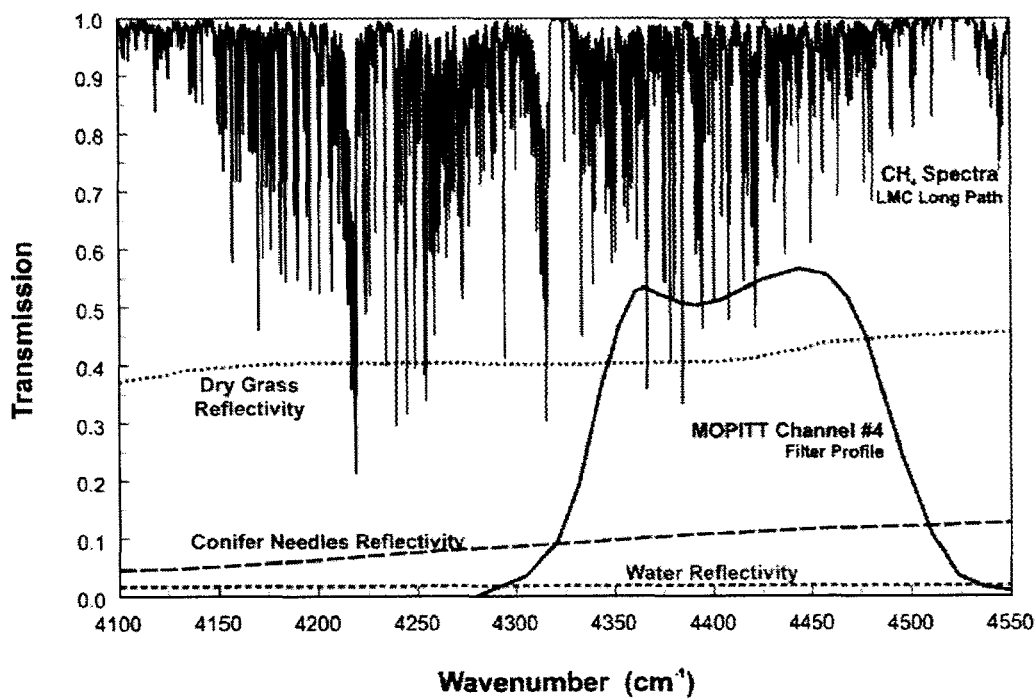
FIG. 7 is a graph of the passband of the MOPITT $CH_4$ channel.

FIG. 1A through 1E show the hemispheric surface reflectivity of many different surface types (from 2 to 4 µm, or 2500 to 5000 $cm^{-1}$)[1]. In the solar channels of MOPITT, surface reflectivity is relatively high for most surface types, except water. However, the slope and shape of the reflectance does vary. FIGS. 6 and 7 show the LMR long-path cell transmission spectra (2 cm gas path length), the filter transmission profile, and the surface reflectivity curves for dry grass, conifer needles, and water. The differences in the magnitude, slopes and shapes of the reflectance curves over the passbands of the channels are easily seen.

Tables 1 and 2 summarize the results of the calculations to determine the effects of varying surface types on the solar GFCR measurements of MOPITT. The tables show the $S_{dif}/S_{avg}$ for a number of different surface reflectance and atmospheric gas concentration conditions. The first row is for the "nominal" condition (100 ppb CO or 1.7 ppm $CH_4$, and a constant 5% surface reflectivity). The second row shows that change in $S_{dif}/S_{avg}$ due to a 10% change in the atmospheric CO concentration (+10 ppb) or 1% change in the $CH_4$ concentration (+17 ppb). These results provide the levels of accuracy in $S_{dif}/S_{avg}$ for CO and $CH_4$ required to meet the design goals of the MOPITT. The next eight rows of the tables show the calculated change in $S_{dif}/S_{avg}$ for the different surface types. Also shown in the right-most column is the error (or uncertainty) in terms of the retrieved atmospheric CO or $CH_4$ concentrations. For the MOPITT solar CO channel described in Table 1, only the errors introduced due to tree leaves and needles are larger than the accuracy goal for CO. This is due primarily to the passband for the MOPITT SW CO being quite narrow and that the slopes (and shapes) of the reflectance curves are fairly flat, see FIG. 1A through 1E and FIG. 6. Of the surfaces modelled, only tree leaves and needles have a significant slope over the passband.

The results for the MOPITT solar $CH_4$ channel described in Table 2 show that most of the surface types tested produce errors larger than the accuracy goal for $CH_4$. This is due to the passband being much wider than the CO channel and there being more structure in the surface reflectance curves over the passband, see FIG. 1A through 1E and FIG. 6. Consequently, surface reflectance must, in this embodiment, be considered to improve the accuracy of surface-viewing trace gas remote sensing of the atmosphere with a GFCR.

Simulated Errors in RealSens™ Retrievals

Figure 8:
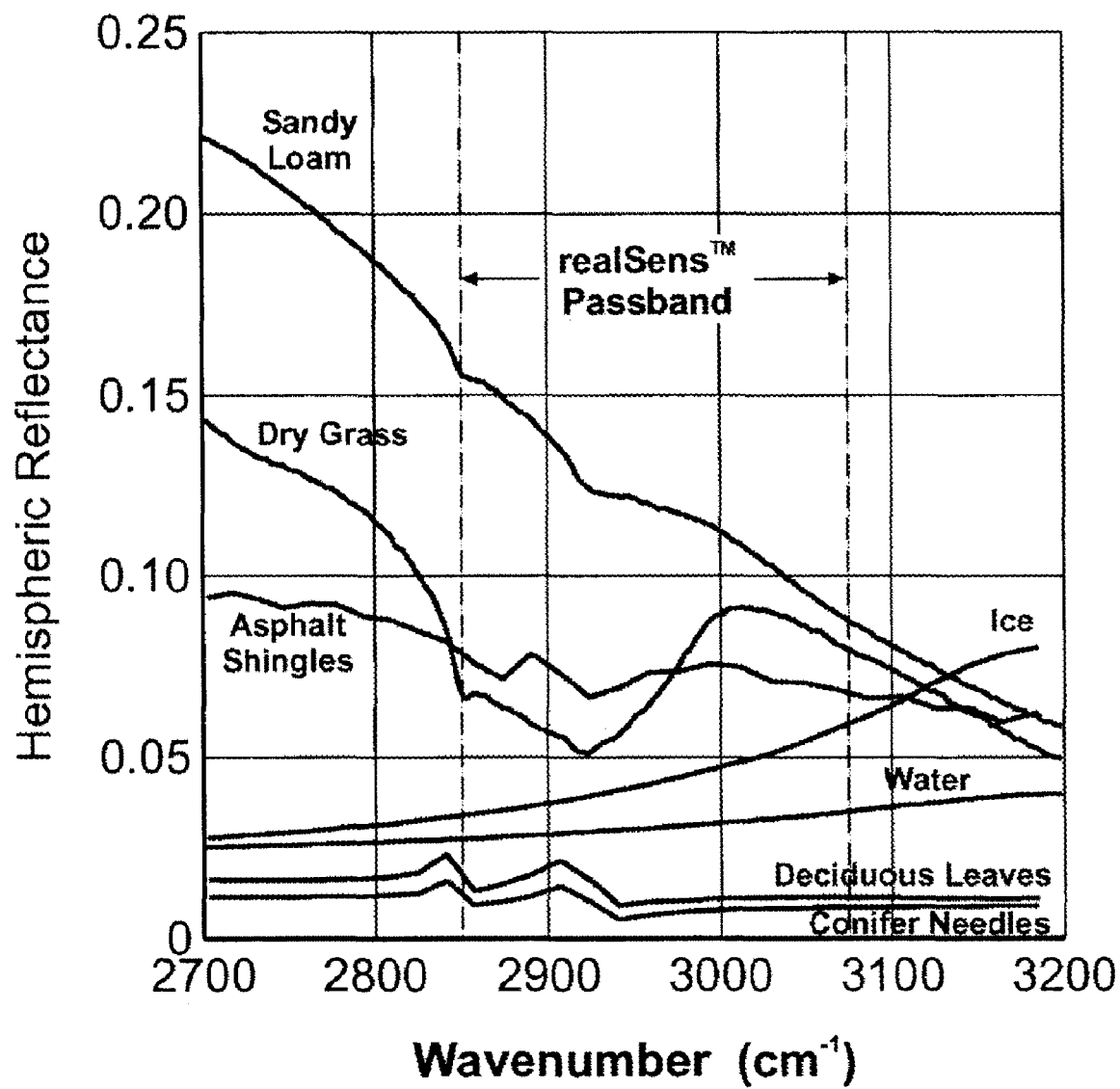
FIG. 8 is a graph of the RealSens™ passband.
Figure 9A:
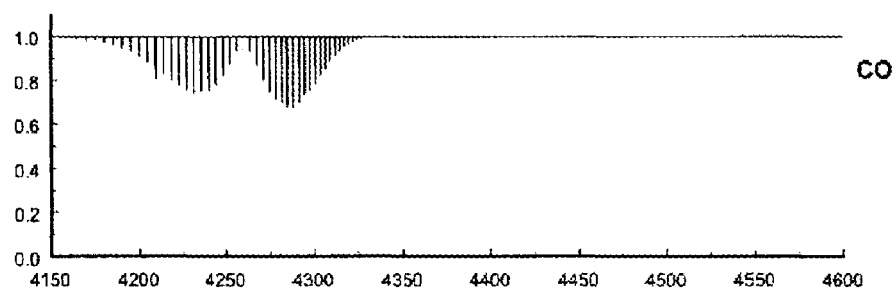
FIG. 9A is a graph of the atmospheric transmission of CO.
Figure 9B:
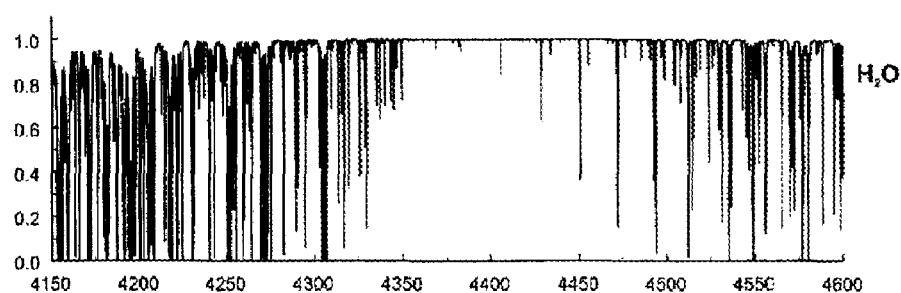
FIG. 9B is a graph of the atmospheric transmission of $H_2O$.
Figure 9C:
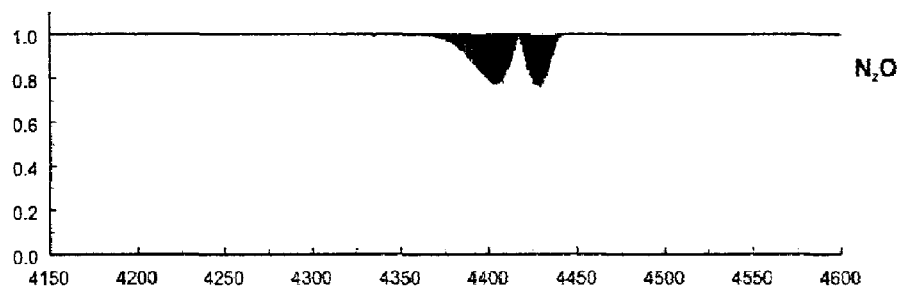
FIG. 9C is a graph of the atmospheric transmission of $N_2O$.
Figure 9D:
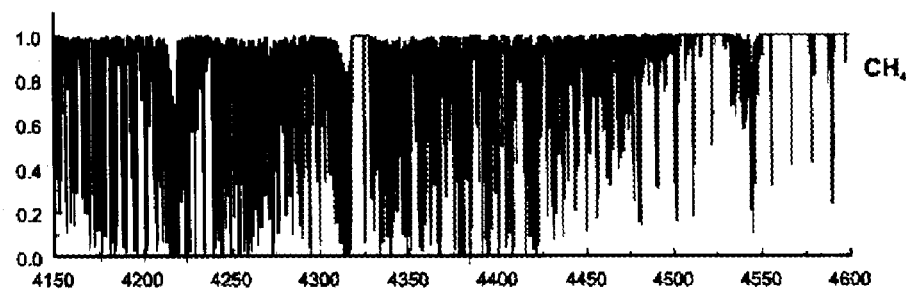
FIG. 9D is a graph of the atmospheric transmission of $CH_4$.
Figure 9E:
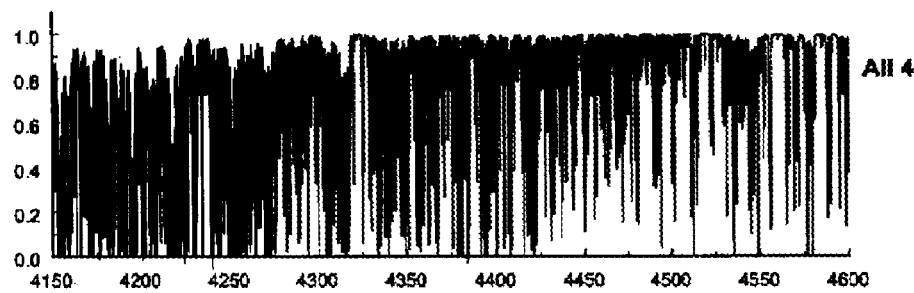
FIG. 9E is a graph of the atmospheric transmission of CO, $H_2O$, $N_2O$, $C_4$ superimposed.
Figure 9F:
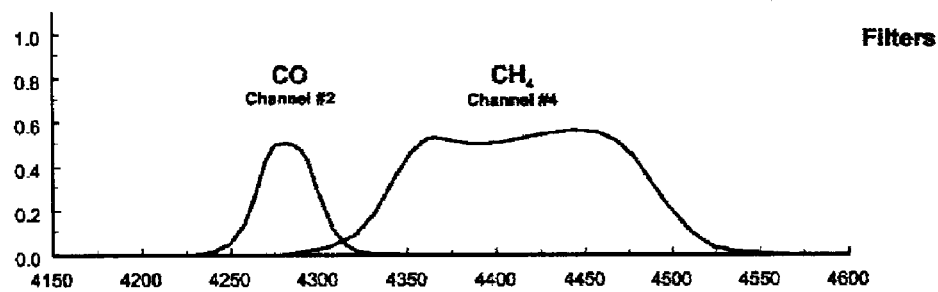
FIG. 9F is a graph of the CO and $CH_4$ passband filters.
Figure 10:
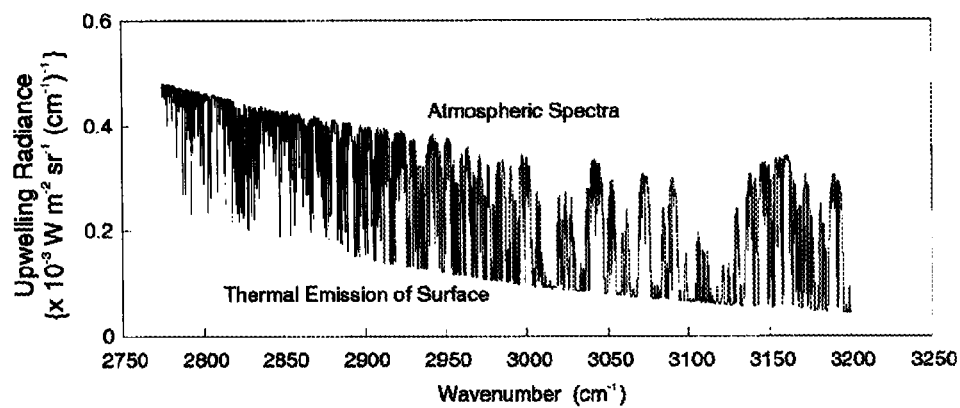
FIG. 10 is a graph of the calculated atmospheric spectra including the thermal emission of surface.

RealSens™ is an aircraft-based GFCR remote sensing instrument designed to detect the presence of leaked natural gas (NG) near the surface. RealSens™ measures ethane ($C_2H_6$) in the 2850 to 3075 $cm^{-1}$ range (3.25 to 3.51 µm), using a SVCR. For RealSens™, the issue of varying surface types are potentially more significant than for MOPITT. First, the spectral band is quite wide (250 $cm^{-1}$). Second, in this spectral region, variations in surface reflectivity over the passband are very large, as can be seen from FIG. 8. Third, in the spectral region, unlike the MOPITT solar channels, radiation emitted by the surface is a significant component in the upwelling radiance. FIG. 10 shows calculated atmospheric spectra within the spectral region, including the thermal emission from the surface. Table 3 lists many of the atmospheric, environmental and instrument parameters used in this model calculation, some of which are constant and some of which are the nominal values (and are varied in this analysis).

Table 4 summaries the results of these calculations (a parametric analysis) to determine the effects of varying surface types and variations in other parameters on RealSens™. The tables shows the calculated $S_{dif}/S_{avg}$ of a number of different surface types and atmospheric and environment conditions. The first row is for the "nominal" condition (no leaked $C_2H_6$ in the FOV and constant 5% surface reflectivity). The second row is for a +10 ppm-m leak of $C_2H_6$ at the surface. The next eight rows of the tables show the calculated change in $S_{dif}/S_{avg}$ for different surface types and other variations. Also shown is the error (or uncertainty) in terms of the retrieved $C_2H_6$ concentrations of the different surface types. For the RealSens™, this effect is very large, greatly reducing the accuracy of $C_2H_6$ leak detection.

In summary, the expected variance in the "in-band" surface reflectivity is highly dependent on the wavelength of the GFCR passband. The larger the expected variance, the greater the potential GFCR retrievals errors. Also, since the reflectance curves do not vary rapidly with wavelength, then the wider the passband of the GFCR, the greater the likelihood of surface reflectance variations to induce errors in the GFCR retrievals. Similarly, the narrower the passband, the smaller the potential errors.

Utility of Multi-Spectral Data with GFCR Retrievals

To resolve the problem of spectrally varying upwelling radiance in retrievals from nadir-viewing GFCRs, the surface reflectivity spectral profile of the target area is determined, either by measurement, or estimation, or a combination. The signals produced by a GFCR, which are based on the received reflected radiation in a selected passband, are then analyzed with the surface reflectivity spectral profile to determine the presence of a target gas.

Figure 11:
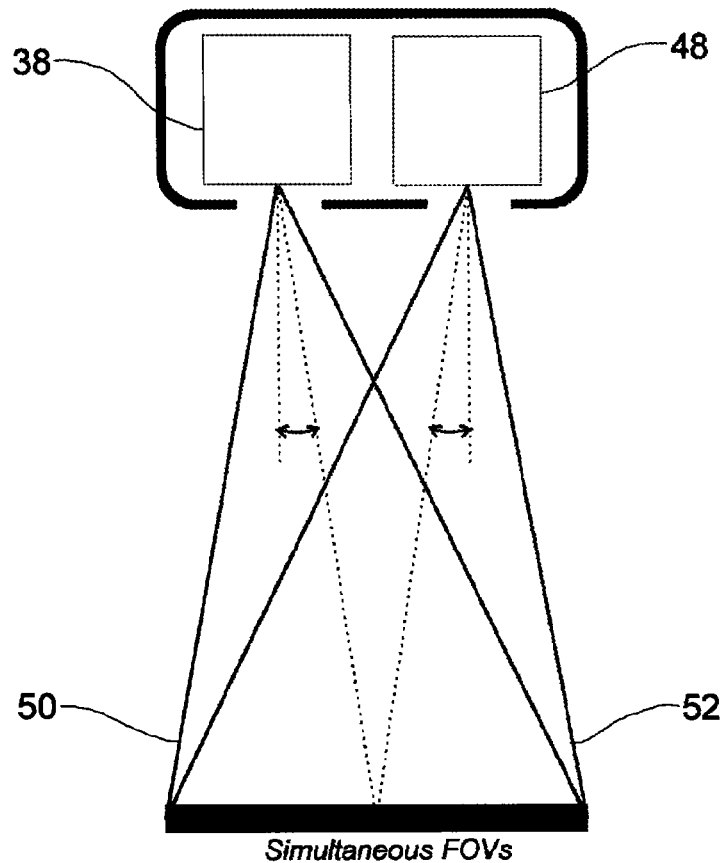
FIG. 11 is a schematic of an optical configuration of a GFCR and a spectrometer with simultaneous fields of view.

In one example, simultaneous (both temporally and spatially) spectral measurements of the upwelling radiance may be used to correct the signal from a GFCR. Simultaneous measurements simplify matters by reducing errors without increasing the amount of necessary calculations, however other strategies may also be employed. Simultaneous spectral measurements may be taken using an ancillary imaging spectrometer 48. An imaging spectrometer is a spectrometer that provides spatial as well as spectral information. FIG. 11 shows a configuration for such an instrument combination, providing simultaneous field-of-views (FOVs) 50 and 52 for both the GFCR 38 and the multi-spectral imaging spectrometer 48, or hyper-spectrometer.

The device as shown in FIG. 11 depicts the GFCR 38 and the spectrometer 48 as separate elements. In other embodiments, the spectrometer and the GFCR may be separate devices, may be contained within a single apparatus, or may share at least one converter of light to electrical energy. It will be understood that the function of the ancillary spectrometer 48 may be incorporated into the GFCR 38, as will be discussed below with reference to FIG. 19. In the example shown, spectral measurements from the imaging spectrometer 48 provide information on the spectral distribution of the upwelling radiation over a wide spectral band, including the passband of the GFCR 38. This information is used in the GFCR data retrieval for removing the effects of spatial variations in the surface reflectivity. In operation, the required number of spectral channels in the imaging spectrometer 48 across the passband of the GFCR 38 to perform these retrievals is determined either experimentally or by models. In the analysis presented below, there are 10 multi-spectral channels across the RealSens™ passband (25 cm$^{-1}$ resolution). In the following sections, the utility of ancillary multi-spectral data for retrievals in the RealSens™ GFCRs is described using the instrument depicted in FIG. 11.

In this embodiment, the methodology by which simultaneous multi-spectral data is used to correct GFCR retrievals for surface reflectance variations is designed to handle a wide range of measurement conditions. These include:

(1) If, {a} the gas being measured by the GFCR has a significant natural background concentration, or {b} the gas being measured has a sparse absorption band (ie. only a few well-spaced absorption lines, like CO), or {c} the expected variations in the amount gas being measured is small (ie. the variations in the amount of energy absorbed by the gas is small), then the measured upwelling radiance is, to first order, not affected by the variation in the radiative absorption by the gas of interest. In this case, the retrieval of surface reflectivity from the multi-spectral data and the retrieval of trace gas concentration can be considered independent.

(2) If the expected variation in the absorption by the gas of interest is large, then the potential effects of gas concentration on upwelling radiance are preferably considered. This is the case if the expected variations in the concentration of the gas of interest are substantially and/or if the gas of interest has a strong absorption band. In this case, the retrieval of surface reflectance and trace gas concentration are not independent of each other.

(3) Variations in other parameters, such as surface temperature and absorption by other gases (other than the gas of interest) may cause variations in the upwelling radiance over the passband. Consequently, the retrieval algorithm preferably must be insensitive to uncertainty in these parameters. For example, if the wavelength of the GFCR passband is long enough that thermal emission becomes a significant component of upwelling radiance, then a simultaneous measurement of the surface temperature may be required. Effects of thermal emission may be removed by subtracting the effects from the received radiation.

Figure 12:
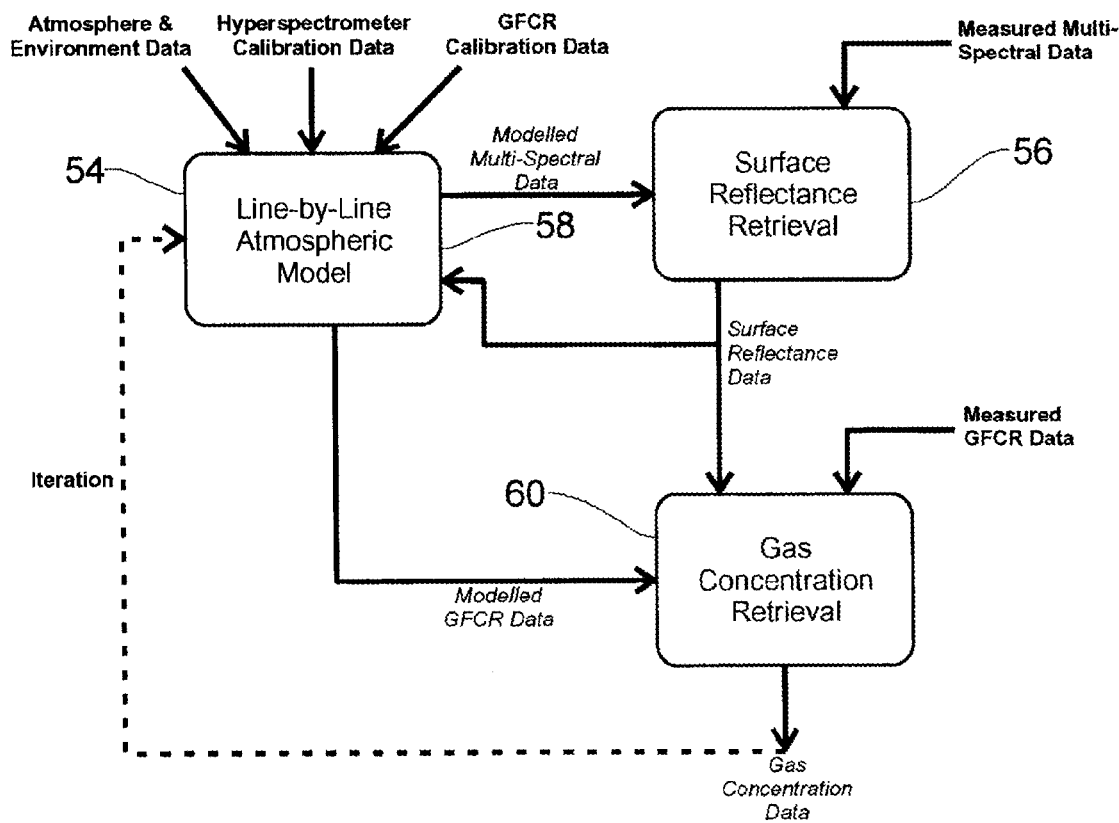
FIG. 12 is a flow diagram of a method of detecting the presence of a target gas.

A preferred methodology for GFCR trace gas retrieval using ancillary multi-spectral data is highlighted in a flow chart in FIG. 12. At the centre of this methodology is an atmospheric radiative transfer model which utilises a general line-by-line integration code. Any number of existing codes could be used. This model allows the calculation of theoretical radiances in the atmosphere, including sources (Sun and thermal emission), absorbers (absorbing gases) and scatterers (reflecting surface). This model is used throughout the retrievals. The first stage of the retrieval, which includes steps 54 and 56, is to retrieve the surface reflectance in the FOV from the multi-spectral data. In step 54, the atmospheric radiative transfer model is used to calculate hypothetical imaging spectrometer signals as a function a range of surface reflectivities. This is preferably done over all spectral channels. Inputs to this step preferably include measured (or weather forecast model) data for the atmosphere (including vertical temperature, pressure, humidity, and any radiatively active gas concentration profiles), the environment (including surface temperature, Solar radiance at the top of the atmosphere, SZA, and surface angle), and the instrument (including the imaging spectrometer temperature and calibration data). The output of this step is a lookup-table of hypothetical imaging spectrometer signals (ie. multi-spectral data) as a function of the surface reflectivity, in each band or channel of the imaging spectrometer. Step 56 compares the measured multi-spectral data to the lookup-table, retrieving (by interpolation of the lookup-table) the surface reflectivity in each channel of the imaging spectrometer (ie. as a function of wavelength, at the spectral resolution of the imaging spectrometer).

The second stage of the retrieval, including steps 58 and 60, is the retrieval of the trace gas concentration. In step 58 the same atmospheric radiative transfer model from step 54 is used to calculate hypothetical GFCR signals as a function a range of concentrations of the trace gas of interest in the FOV. In this step, the model inputs are similar to step 54, but also include the retrieved surface reflectivity curves from step 56 plus information about the GFCR (including GFCR temperature, pressure and calibration data). The output of this step is a lookup-table of GFCR signals as a function of trace gas concentration. Step 60 compares the GFCR lookup-table to the measured GFCR signals, retrieving (by interpolation of the lookup-table) the trace gas concentration.

The third and final stage to the retrieval algorithm is to iterate steps 54 through 60, if necessary. If, as stated previously, the expected variation from the natural background of the trace gas produces a significant change in the upwelling radiance, then by iterating the retrieval process, and including the previously retrieved trace gas concentration in the atmospheric radiative transfer model, the retrieval accuracy is improved. This step may not be necessary if the retrieved variation in the trace gas (relative to the background) is small.

The details of the operational retrievals may in some embodiments be more complex than stated above, as the lookup-table would not be calculated for each pixel of GFCR data (due to constraints in computer power). Consequently, the lookup-tables calculated may in some embodiments be a function of more parameters or variables than stated. These could include surface temperature, SZA, and atmospheric pressure, temperature and humidity. Also, depending on the accuracy of the atmospheric radiative transfer model, it may be necessary to minimize the input of the model in the retrievals and utilize the instrument calibration and/or validation measurements (imaging spectrometer and GFCR). In this case, the model is only used to modify a calibration measurement from its nominal conditions (or parameters) to the conditions of the measurement, thus minimizing any systematic errors introduced by the atmospheric radiative transfer model.

It will be understood that retrieval of a surface reflectivity profile using multi-spectral measurements may be performed by comparing the measured multi-spectral data to the results of an atmospheric radiative transfer model as described above. Retrievals may also be performed by comparing the measured multi-spectral data to the results of calibration measurements of surfaces of known reflectivity with or without using the radiative transfer model. Thus, calibration measurements may be obtained by flying an imaging spectrometer across a known ground surface and making calibration measurements. Further, retrievals may also be performed by comparing the measured multi-spectral data to a combination of both models and calibrations. When choosing a method, a factor to consider is which method would provide the greater accuracy in the retrievals.

Concepts for a Multi-Spectral GFCR

Figure 1A:
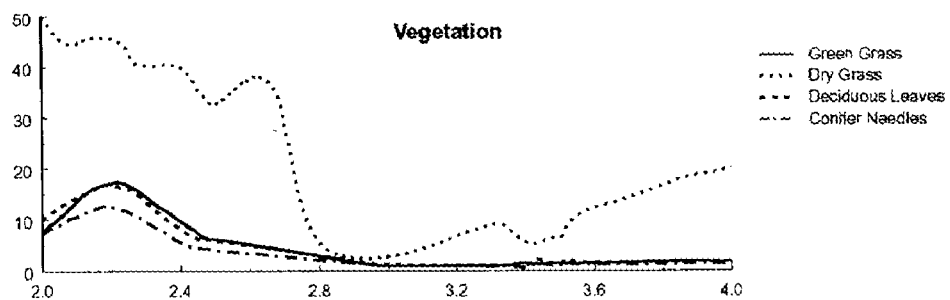
FIG. 1A through 1E are graphs of the surface reflectivity of selected materials.
Figure 1B:
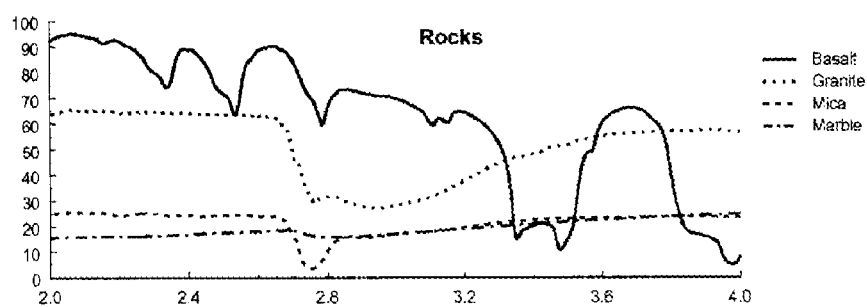
Figure 1C:
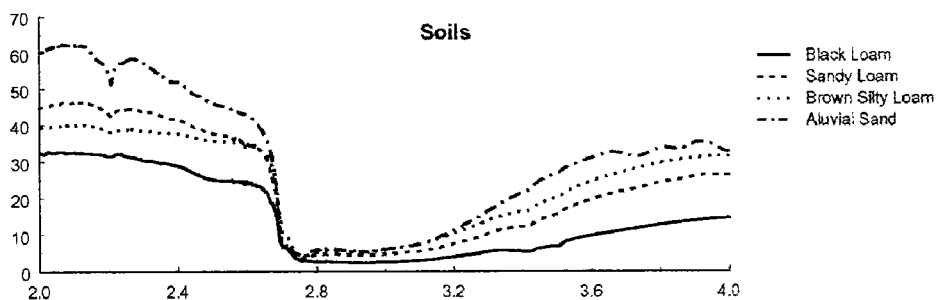
Figure 1D:
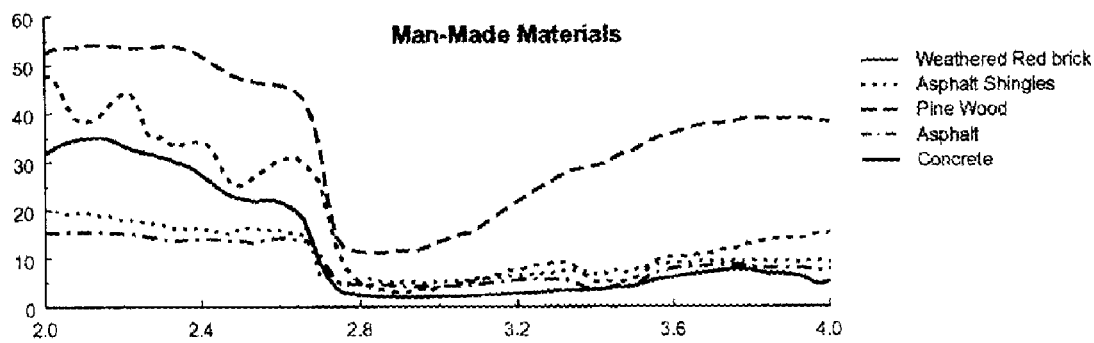
Figure 1E:
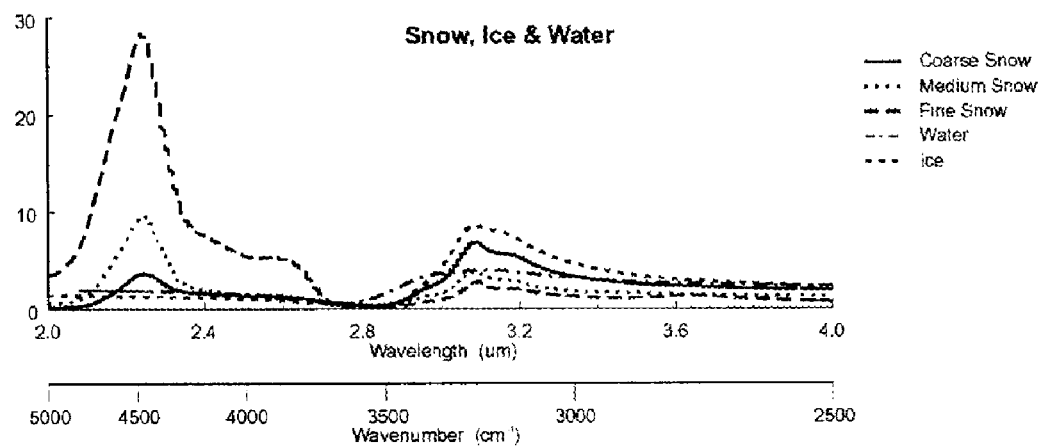
Figures 2A, 2B, 2C, 2D:
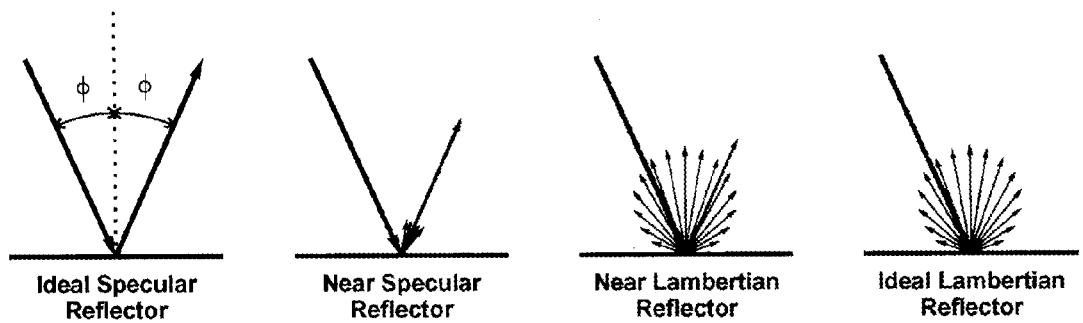
FIG. 2A through 2D are graphs depicting the response of different types of reflectors on the surface reflectivity.
Figure 3:
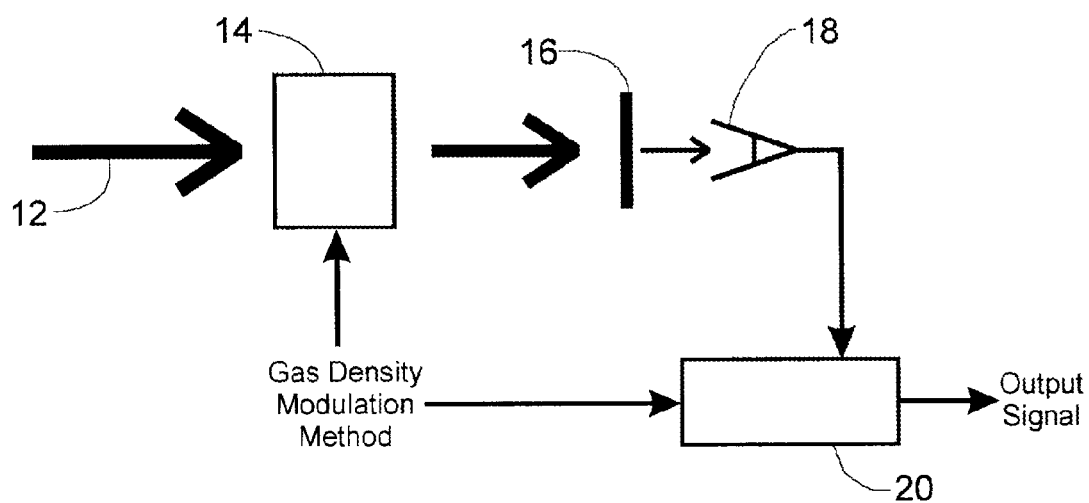
FIG. 3 is a schematic of a gas-filter correlation radiometer (GFCR).
Figure 4:
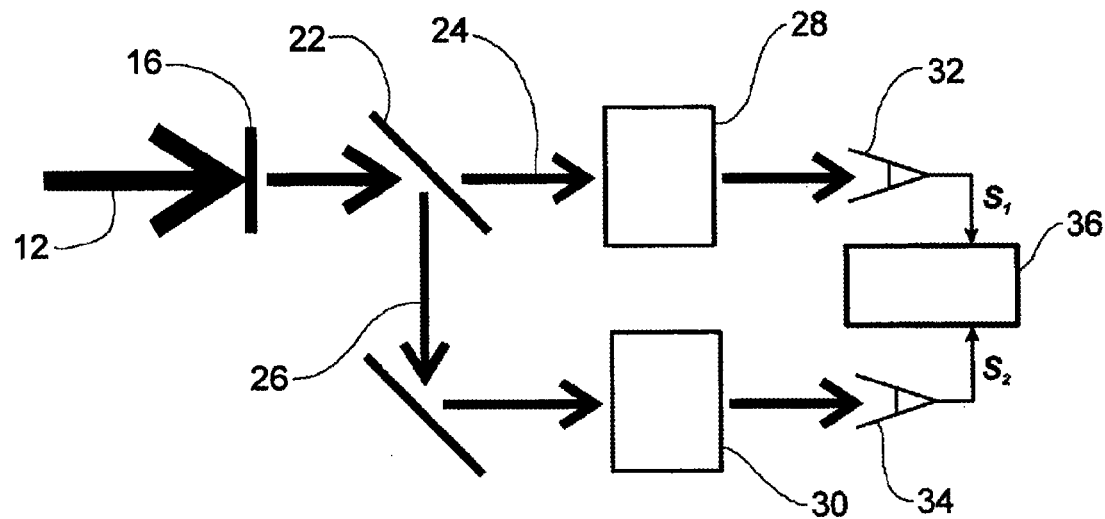
FIG. 4 is a schematic of a simultaneous-view correlation radiometer (SVCR)
Figure 5:
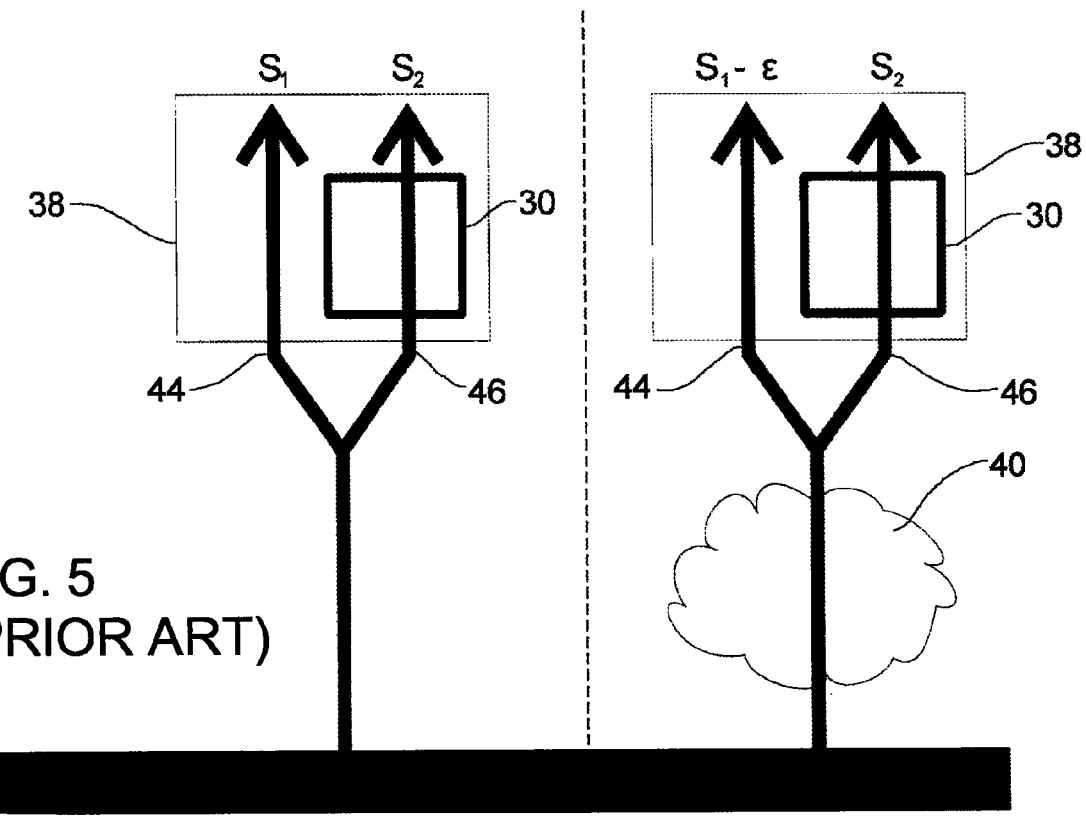
FIG. 5 is a schematic depiction of the GFCR principle.
Figure 17:
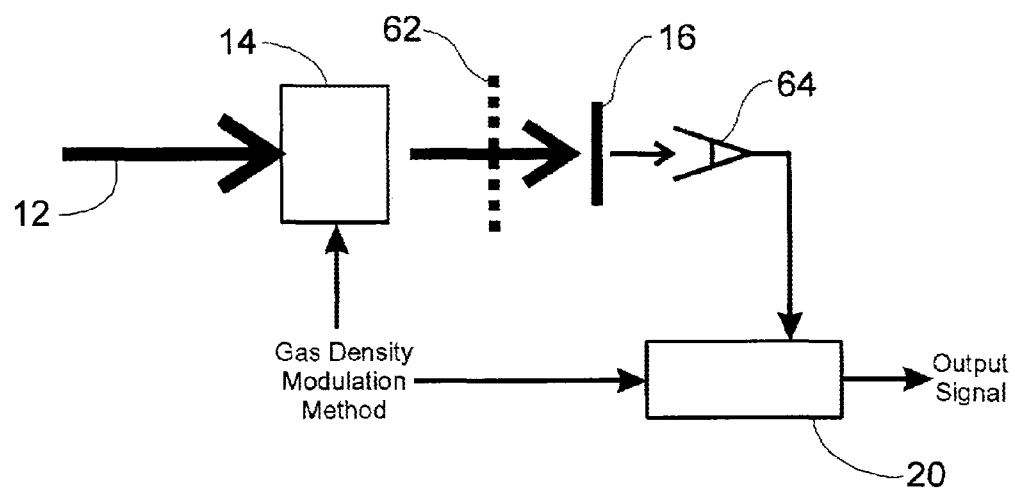
FIG. 17 is a schematic of a multi-spectral gas-filter correlation radiometer.

Two general designs by which multi-spectral data could be combined with GFCR include (1) mounting two separate instruments into one unit, and ensure that they are aligned to provide simultaneous FOVs, as depicted in FIG. 11, and (2) combining the two instruments into one to achieve a multi-spectral GFCR. Referring to FIG. 17, this could be done by introducing a spectrally dispersive element 62, such as a prism, grating, or grism, into the GFCR chain and replacing the IR detector 18 shown in FIG. 3 with a focal plane array (FPA) 64, which is a 1- or 2-dimensional array of detector pixels. By doing so, the incoming radiation is dispersed spectrally in one dimension of the FPA (ie. the spectral dimension). A GFCR signal can be calculated by adding the pixels (or some of the pixels) in the row in the spectral dimension, covering the passband of the GFCR.

Figure 18:
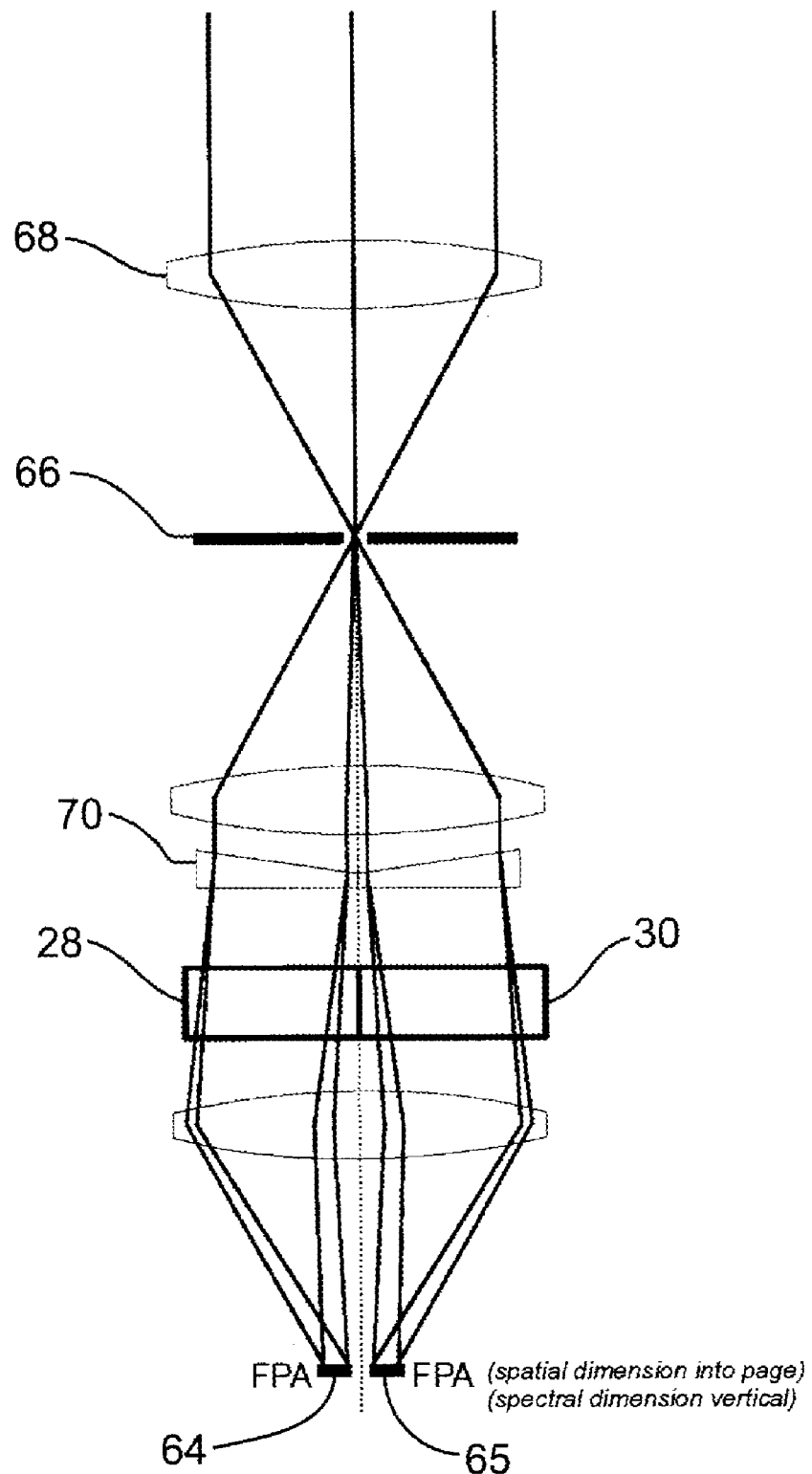
FIG. 18 is a schematic of the optics in an alternate multi-spectral gas-filter correlation radiometer.
Figure 19:
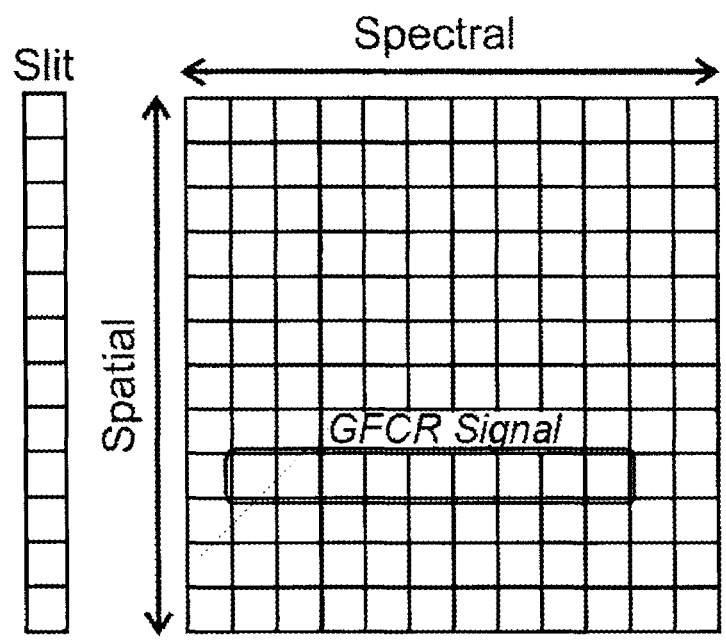
FIG. 19 is a schematic showing spatial and spectral dimensions of a focal plane array that may be used as a detector.

FIG. 18 shows a conceptual design for an imaging multi-spectral GCFR. This design is based on the current design of the RealSens™ instrument. RealSens™ uses a bi-prism along a single optical chain to biaxially separate the two optical channels of the GFCR. In this model, the optics are changed to create a re-imaging system, with a slit 66 at the focal point of the fore-optics 68 to define the FOV of the instrument. On the bi-prism 70, which biaxially separates the two channels, a transmission grating coating is applied, forming a bi-grism (a combination of a prism and a grating). The detectors are then replaced by two 2-dimensional FPAs 64 and 65. Consequently, the optical separation of the two channels and spectral dispersion can be achieved simultaneously. Referring to FIG. 19, since the system is re-imaging, the slit 66 (and therefore the FOV) is imaged onto one dimension of each FPA 64 and 65 (providing a spatial information along one dimension of the FPA), whilst the energy passing through the slit 66 is dispersed as a function of wavelength across the other dimension of the FPA 64 and 65. The coating of grating 70 is designed to disperse the passband (or slightly wider) of the GFCR across one axis of the FPA 64 or 65. GFCR signals in turn can be calculated by adding some (or all) of a row of pixels along the spectral axis. In this configuration, the multi-spectral GFCR can be operated in a pushbroom imaging mode.

Note that, if the pixel dimensions are very small, it may be advantageous to bin pixels into larger pseudo-pixels. For example, one pseudo-pixel may consist of 5×4 individual pixels. As such, instead of a GFCR signals coming from a single row of pixels, it may come from a row of pseudo-pixels. Continuing with the example, if GFCR signal comes from 10 pseudo-pixels, then 200 individual pixels would be added.

In another embodiment, it may not be necessary to utilise a transmission grating coating to provide spectral dispersion in the multi-spectral GFCR. Instead, the bi-prisms 70 themselves could provide spectral dispersion. In this case, the bi-prism is designed from a material with a significant spectral dispersion at the wavelengths of the GFCR passband.

Figure 20:
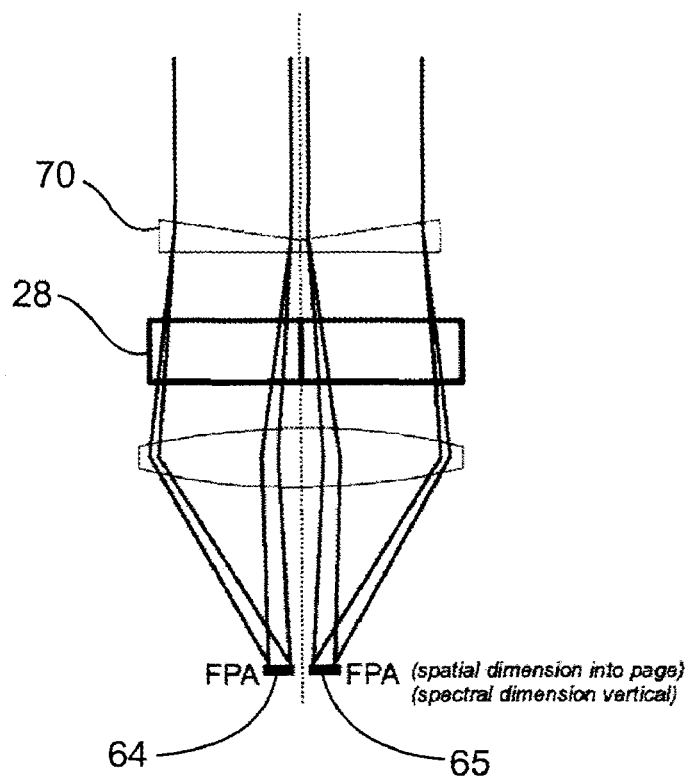
FIG. 20 is a schematic showing an embodiment of optics that may be used in a multi-spectral gas-filter correlation radiometer.

In another embodiment, referring to FIG. 20, the multi-spectral GFCR need not be re-imaging. In such a case, one axis of the FPA provides spatial information only, and the other axis provides a convolution of spatial and spectral information. As a consequence, data retrieval is more complicated, as the spectral and spatial information are combined along one axis of the FPA. However, such an instrument is optically less complex (and smaller).

Details of Radiance Model Used for Calculations

Figure 21:
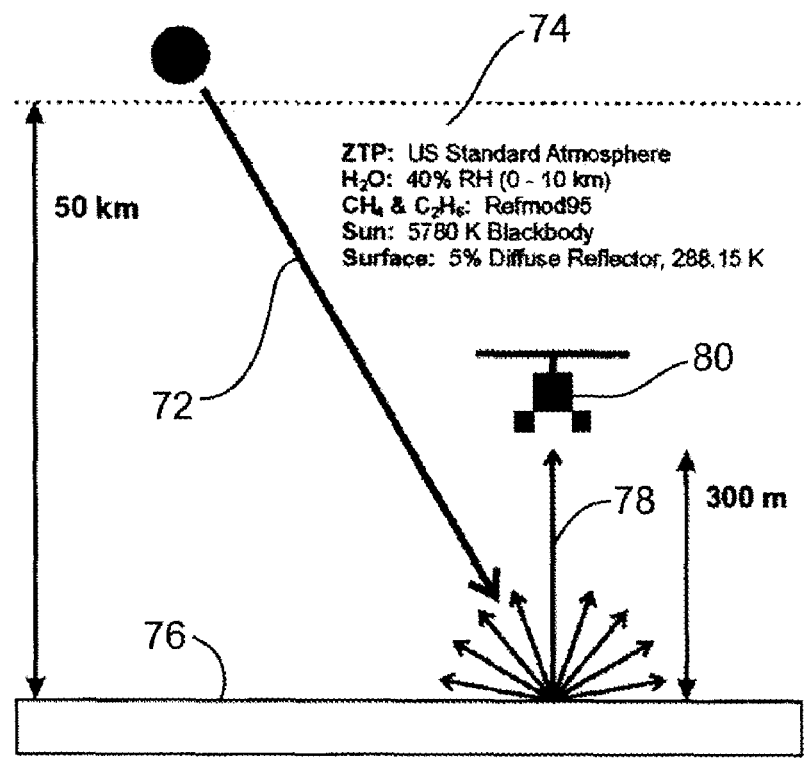
FIG. 21 is a schematic showing a radiance model.

The results of calculations of upwelling atmospheric radiance are discussed above. These calculations are based on the results of a general line-by-line integration program known as Genspect, and spectral line data from the Hitran 2004 molecular line database. Table 6 details the atmospheric, environmental and instrument parameters (and defaults) used in this document. The details of the radiance model are as shown in FIG. 21. Solar radiation 72 passes down through the atmosphere 74, and is absorbed by species in the atmosphere 74. It is reflected by the surface 76, which also emits thermal radiation. The reflected and thermal radiation 78 then upwells through the atmosphere toward the aircraft 80, and is once again absorbed by the atmosphere. FIG. 1A through 1E show the hemispheric reflectance over the 2 to 4 µm regions.

Figure 22:
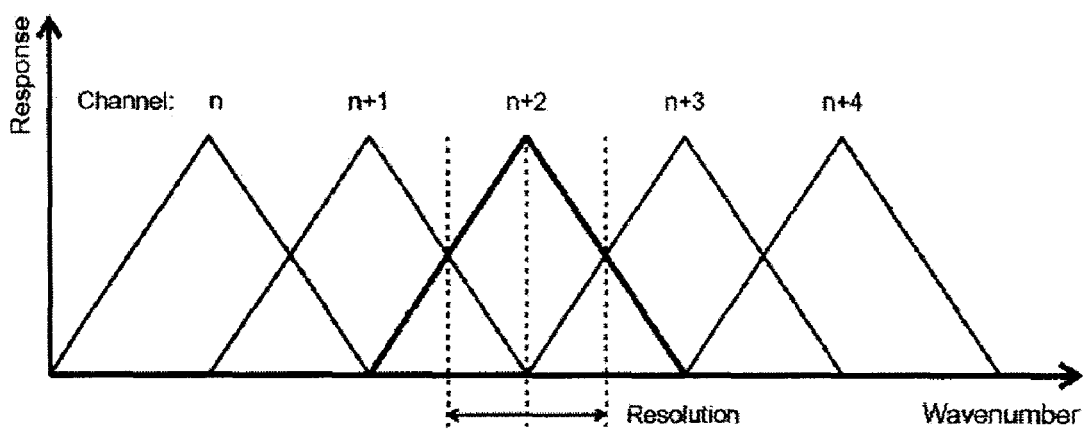
FIG. 22 shows triangular shaped instrument response curves for a gratings based hyperspectral radiometer.

The theoretical response of a imaging spectrometer was calculated by convolving a triangular-shaped instrumental response function with the calculated radiances. FIG. 22 shows a typical triangular-shaped instrument response curves (ie. the instrument function) for a grating-based imaging spectrometer. These curves define the spectral resolution of the instrument.

Like all spectrometers, an imaging spectrometer does not provide perfect monochromatic spectra. Instead it provides a measurement of the radiation field over a narrow passband. The width of the passband determines how fine of features which can be resolved. For a typical infrared imaging spectrometer, the resolution is enough to resolve an absorption band, but not enough to resolve individual absorption lines.

Example

This section describes a hypothetical example of a GFCR retrieval using the methodology described in section 3.1 using the device depicted in FIG. 11. This example is for a retrieval of leaked $C_2H_6$ concentrations near the surface with the RealSens™ instrument. This example is more complex than a remote sensing measurement at a shorter wavelength (higher wavenumber), such as the MOPITT solar channels, because at these wavelengths, thermal emission is a significant component of the upwelling radiation.

Figure 13A:
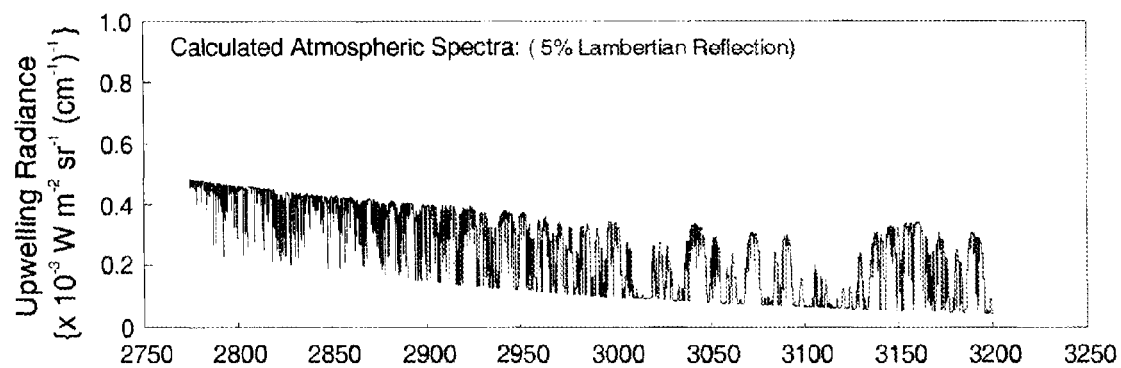
FIG. 13A is a graph of a calculated atmospheric spectra assuming a uniform 5% surface reflectance.
Figure 13B:
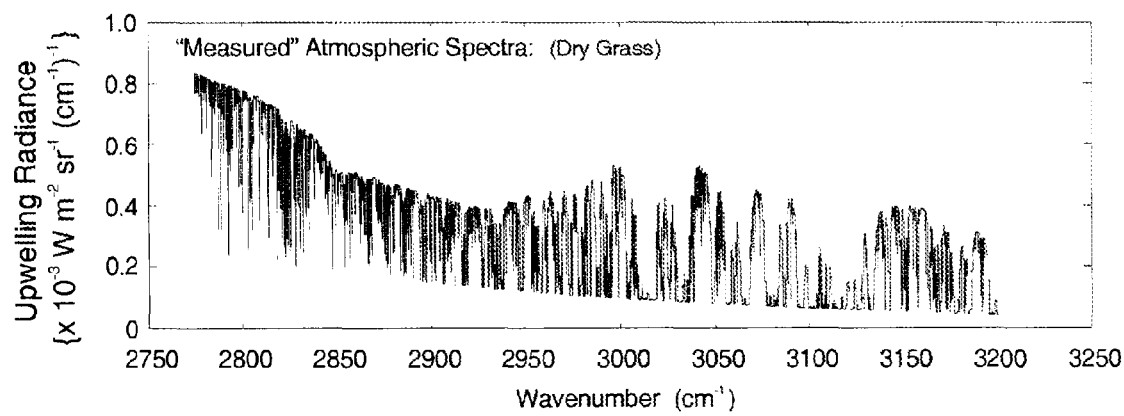
FIG. 13B is a graph of a measured atmospheric spectra assuming a dry grass reflectance.
Figure 14:
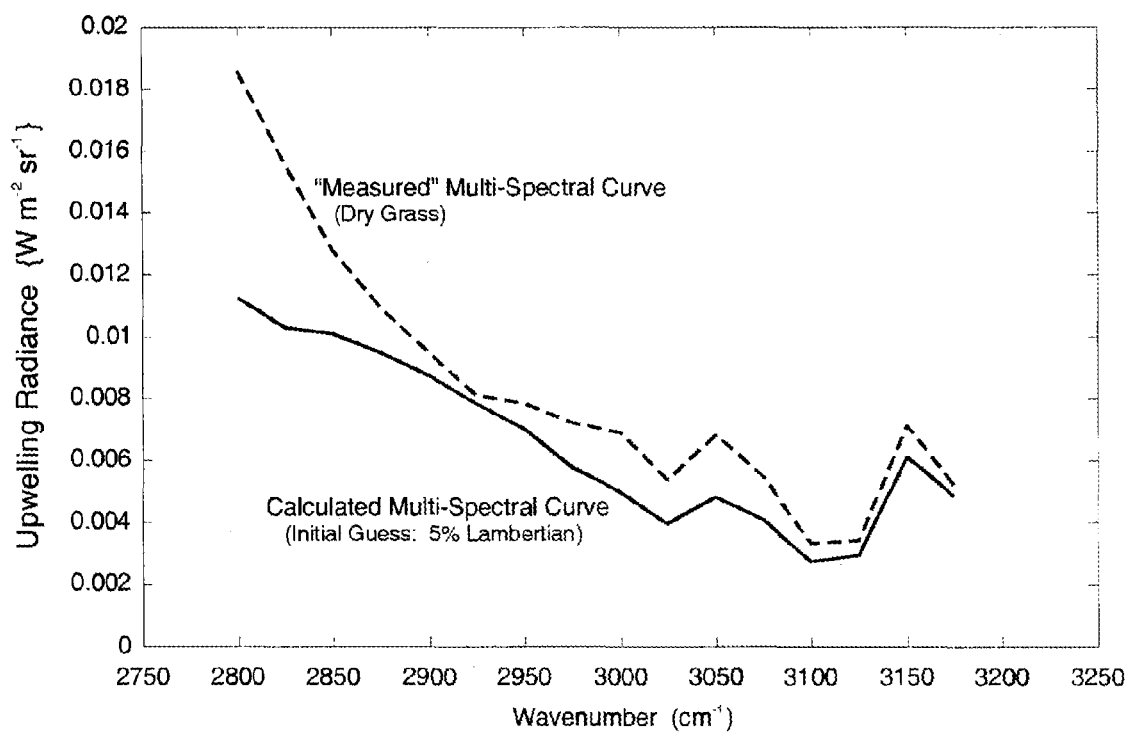
FIG. 14 is a graph of the upwelling radiance of a uniform 5% surface reflectance and a dry grass reflectance.
Figure 15:
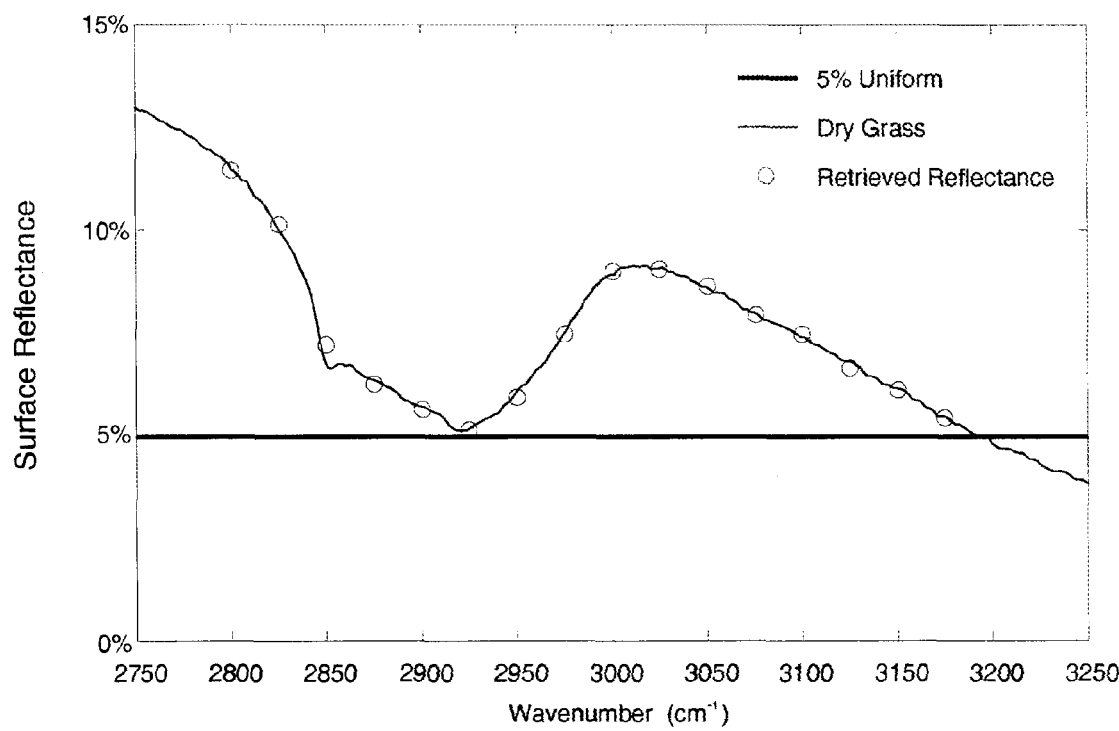
FIG. 15 is a graph of the surface reflectance of a uniform 5% surface reflectance, dry grass reflectance, and retrieved reflectance.

In this example, there are a number of assumptions about the instrument, the atmosphere and the environment. Table 3 lists many of these parameters, some of which are constant and some of which are the nominal values (and are varied in this analysis). FIGS. 13A and 13B show results of two model calculations of upwelling radiance reaching the RealSens™ aircraft. FIG. 14A shows the upwelling radiance assuming a uniform 5% surface reflectance, and FIG. 14B shows the upwelling radiance assuming a "dry grass" lambertian surface reflectance. For this analysis, it is assumed that FIG. 14B represents the "measured" upwelling radiance, for which the surface reflectivity will be retrieved. FIGS. 14A and 14B show the hypothetical calculated and "measured" multi-spectral curves (assuming a spectrometer resolution of 25 cm$^{-1}$). By comparing the two curves, an estimate of the surface reflectance across the passband can be calculated. FIG. 15 shows the initial guess surface reflectance of 5% uniform (thick line), the "measured" reflectance of dry grass (thin line), and the retrieved reflectance data (circles).

Figure 16:
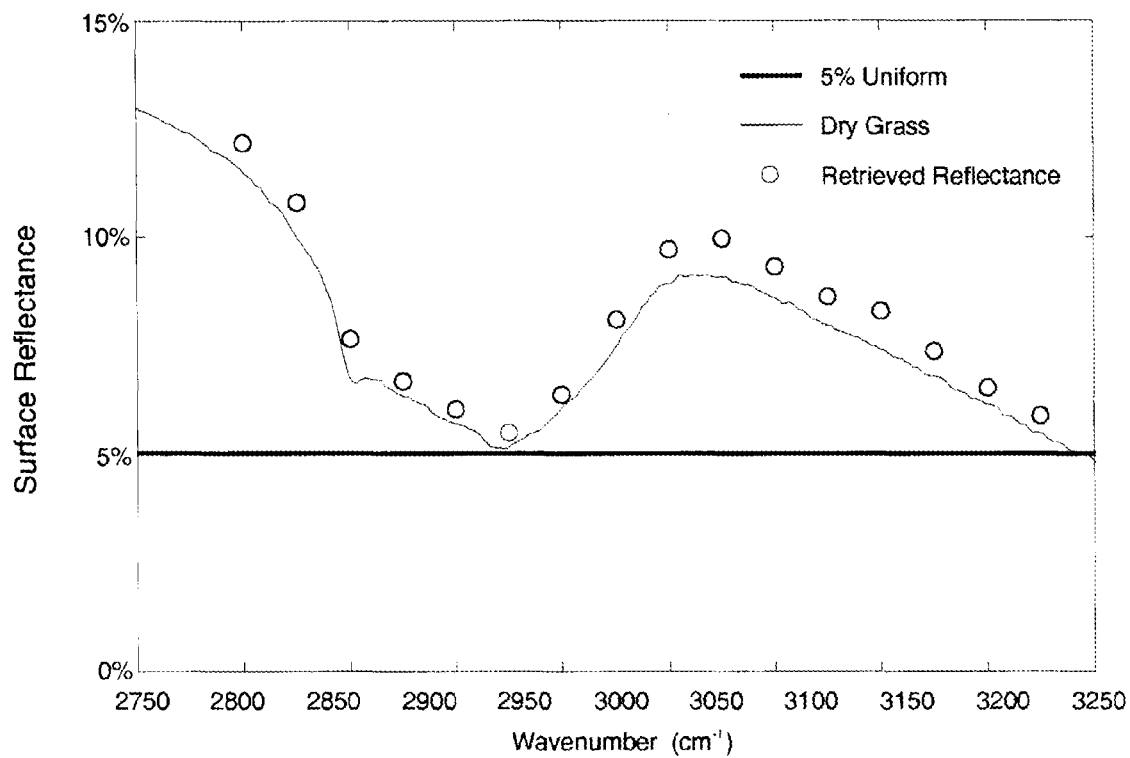
FIG. 16 is a graph of the surface reflectance of a uniform 5% surface reflectance, dry grass reflectance, and retrieved reflectance, with the surface zenith angle in the atmospheric radiative transfer model being 5° too large.

As expected, the retrieval is very good, as in this parametric analysis there are no other errors or uncertainties. An error in any parameter, such a SZA, vertical water vapour profile, or surface temperature will result in an error in the retrieved surface reflectance. For example, FIG. 16 shows the retrieved surface reflectance in which the SZA in the atmospheric model was off by 5°. In this case the "real" or "measured" SZA was 30°, but SZA parameter in the atmospheric radiative transfer model was 35°. Consequently, the calculated radiances from the model are smaller than the "measured," resulting in a higher retrieved surface reflectance. However, if the same atmospheric radiative transfer model used for the retrieval of surface reflectance from multi-spectral data is also used for retrieval of trace gas concentration from GFCR data, then any systematic low spectral resolution error in the parameters used in the retrieval algorithm is, to first order, minimised. In other words, any systematic error in an input parameter to the model is, to first order, balanced by the resulting error in the retrieved surface reflectivity. As such, sensitivity to errors or uncertainty in many of the parameters in the atmospheric radiative transfer model is minimised.

To illustrate this effect, Table 5 lists the results of a lookup-table RealSens™ retrieval of $C_2H_6$ concentration (ppm-m), using multi-spectral data with a spectral resolutions of 25 cm$^{-1}$. In this parametric study, the existence of "measured" multi-spectral and GFCR data is assumed, and that this "measured" data comes from calculated signals assuming a variation in an input parameter (or two). The "measured" multi-spectral data is then used to retrieve the surface reflectivity over the passband, which is then used to calculate "nominal" GFCR signal (for the nominal atmosphere, environmental and instrument conditions, plus the retrieved surface reflectivity). The first column of Table 5 lists a series of parameters varied from their nominal condition for which the hypothetical "measured" signals are calculated (the nominal conditions for these parameters are listed in Table 3). The second column lists the hypothetical "measured" GFCR signals ($S_{diff}/S_{avg}$). The third column lists the calculated nominal $S_{diff}/S_{avg}$, calculated using the retrieved surface reflectivity from "measured" multi-spectral data. The fourth column lists the difference between the hypothetical "measured" $S_{diff}/S_{avg}$ from the nominal signals. And finally, the fifth column lists the error in GFCR retrieval, expressed in units of ppm-m of $C_2H_6$. The first row of the table lists the change in the GFCR signal as a function of a 10 ppm-m leak of $C_2H_6$ at the surface. This value is used to calculate the effective retrieval errors of the other parameters. The other rows list the change in the $S_{diff}/S_{avg}$ due to errors (or variations) in a number of the parameters used in the atmospheric radiative transfer model. These errors are small and significantly improved over the retrievals without multi-spectral data (in comparison to Table 4). Also, errors in parameters other than surface reflectivity (such as SZA or $H_2O$ concentrations) are significantly reduced. In general, retrieval noise is reduced by, in some cases, approaching two orders of magnitude.

Remote sensing of trace gases concentrations near the surface from an airborne or satellite platform is a difficult problem due to variability of the surface and the lower atmosphere causing variability in the upwelling radiance. Recently, the MOPITT satellite instrument has employed the technique of gas-filter correlation radiometry (GFCR) to measure lower atmosphere carbon monoxide and methane. Also, Synodon Inc. has developed a GFCR-based aircraft instrument known as RealSens™ to detect leaks of natural gas. This description has examined how variability in the surface reflectivity within the passband of a GFCR is a significant source of noise in GFCR retrievals. This is due to the fact that absorption lines of the gas of interest are neither randomly nor uniformly distributed within the passband. As a consequence, variations in the upwelling radiance in different segments of the passband of the GFCR modifies the GFCR signals, inducing errors. It has been shown that this effect produces significant noise/errors in the retrievals of the MOPITT CO and $CH_4$ solar channels and the RealSens™ instrument.

To get around this problem, an imaging spectrometer can be deployed with any surface-viewing GFCR. The imaging spectrometer provides spatially and temporally simultaneous spectral measurements of the upwelling radiance over the passband of the GFCR. This data is used to retrieve the surface reflectivity over the passband, which is then input into the GFCR retrievals. It has been demonstrated that this method significantly reduce the errors introduced by surface variations. For RealSens™, the technique reduces noise in retrievals of near surface $C_2H_6$ due to variations in surface reflectivity by almost two orders of magnitude. Also, it reduces other sources of noise which produce low spectral resolution variations in the upwelling radiance, including SZA and absorption by other atmospheric species.

Immaterial modifications may be made to the embodiments described here without departing from what is covered by the claims.

In the claims, the word "comprising" is used in its inclusive sense and does not exclude other elements being present. The indefinite article "a" before a claim feature does not exclude more than one of the feature being present. Each one of the individual features described here may be used in one or more embodiments and is not, by virtue only of being described here, to be construed as essential to all embodiments as defined by the claims.

TABLE 1

GFCR instrument signals ($S_{diff}/S_{avg}$) in the MOPITT "solar" CO band (channel #2) as a function of different surface reflectance types, and +10 ppb (10%) CO (second row).

| Parameter Varied | $S_{diff}/S_{avg}$ | $\Delta$ ($S_{diff}/S_{avg}$) | Uncertainty (ppbv CO) |
|---|---|---|---|
| Nominal* | 0.033307 | | |
| +10 ppb Co {+10%} | 0.033175 | $-1.3 \times 10^{-4}$ | +10 {+10%} |
| 10% Surface Reflectivity | 0.033308 | $6.6 \times 10^{-7}$ | −0.05 |
| Shingles | 0.033315 | $8.1 \times 10^{-6}$ | −0.62 |
| Dry Grass | 0.033297 | $-1.0 \times 10^{-5}$ | 0.78 |
| Ice | 0.033337 | $3.0 \times 10^{-5}$ | −2.3 |
| Sandy Loam | 0.033346 | $3.9 \times 10^{-5}$ | −3.0 |
| Water | 0.033316 | $8.4 \times 10^{-6}$ | −0.64 |

TABLE 1-continued

GFCR instrument signals ($S_{diff}/S_{avg}$) in the MOPITT "solar"
CO band (channel #2) as a function of different surface
reflectance types, and +10 ppb (10%) CO (second row).

| Parameter Varied | $S_{diff}/S_{avg}$ | $\Delta(S_{diff}/S_{avg})$ | Uncertainty (ppbv CO) |
|---|---|---|---|
| Conifer Needles | 0.033505 | $2.0 \times 10^{-4}$ | −15.0 |
| Deciduous Leaves | 0.033499 | $1.9 \times 10^{-4}$ | −15.0 |

*Nominal case refers to a constant 100 ppb CO and a 5% lambertian surface reflectivity.

TABLE 2

GFCR instrument signal ($S_{diff}/S_{avg}$) in the MOPITT "solar"
$CH_4$ band (channel #4) as a function of different surface
reflectance types, and +17 ppb (1%) $CH_4$ (second row).

| Parameter Varied | $S_{diff}/S_{avg}$ | $\Delta(S_{diff}/S_{avg})$ | Uncertainty (ppbv $CH_4$) |
|---|---|---|---|
| nominal* | 0.059511 | | |
| +17 ppb $CH_4$ {+1%} | 0.059414 | $-9.7 \times 10^{-5}$ | +17 {+1%} |
| 10% Refl | 0.059506 | $-5.0 \times 10^{-6}$ | 0.9 |
| Shingles | 0.059177 | $-3.3 \times 10^{-4}$ | 59 |
| Dry Grass | 0.058761 | $-7.5 \times 10^{-4}$ | 132 |
| Ice | 0.059234 | $-2.8 \times 10^{-4}$ | 49 |
| Sandy Loam | 0.059508 | $-3.3 \times 10^{-6}$ | 0.6 |
| Water | 0.059323 | $-1.9 \times 10^{-4}$ | 33 |
| Conifer Needles | 0.058113 | $-1.4 \times 10^{-3}$ | 246 |
| Deciduous Leaves | 0.058401 | $-1.1 \times 10^{-3}$ | 195 |

*Nominal case refers to a constant 1.7 ppm $CH_4$ and a 5% lambertian surface reflectivity.

TABLE 3

List of nominal and constant parameters used in numerical atmospheric radiative transfer model.

| | Parameter | Value |
|---|---|---|
| CALCULATION | Spectral Range† | 2775-3200 cm$^{-1}$ |
| | Resolution† | 0.005 cm$^{-1}$ |
| SUN | Temperature† | 5780 K Blackbody |
| | Solar Zenith Angle‡ | 30° |
| ATMOSPHERE | Maximum Altitude† | 50 km |
| | Downwelling Layers† | 25 (equal pressure) |
| | Temperature Profile† | US Standard Atmosphere[21] |
| | Pressure Profile† | Hydrostatic Equation |
| | Upwelling layers† | 1 (0 to 300 m) |
| | $H_2O$ Profiles‡ | Troposphere: 40% RH Above: 40 ppm |
| | $CH_4$ Profile‡ | 1.7 ppm constant |
| | $O_3$ Profile: | Refmod95 |
| SURFACE | Reflectivity‡ | 5% lambertian |
| | Temperature‡ | 15° C. |
| HYPERSPECTRAL | Spectral Resolution‡ | 25 cm$^{-1}$ |
| | Instrument Function† | Triangular |
| GFCR | Bandpass† | 2860-3080 cm$^{-1}$ |
| | Correlation Cell Pressure | 7.0 kPa pure $C_2H_6$ |
| | Correlation Cell Length | 5.0 cm |

†constant,
‡nominal

TABLE 4 realSens ™ instrument signal ($S_{diff}/S_{avg}$)
as a function of different surface reflectance types, and
+10 ppm-m leaked $C_2H_6$ (second row).

| Parameter Varied | $S_{diff}/S_{avg}$ | $\Delta(S_{diff}/S_{avg})$ | Error (ppm-m $C_2H_6$) |
|---|---|---|---|
| Nominal | 0.73248 | | |
| $C_2H_6$ = 10 ppm-m | 0.73162 | $-8.6 \times 10^{-4}$ | +10 |
| R = 10% | 0.73029 | $-2.2 \times 10^{-3}$ | +25 |
| R = 'Asphalt Singles' | 0.73104 | $-1.4 \times 10^{-3}$ | +17 |
| R = "Dry Grass" | 0.71651 | $-1.6 \times 10^{-2}$ | +185 |
| R = "Ice" | 0.72308 | $-9.4 \times 10^{-3}$ | +110 |
| R = "Sandy Loam" | 0.73461 | $+2.1 \times 10^{-3}$ | −24 |
| R = "Water" | 0.73109 | $-1.4 \times 10^{-3}$ | +16 |
| $CH_4$ = 1.8 ppm | 0.73237 | $-1.1 \times 10^{-4}$ | +1.3 |
| $H_2O$ = 50% RH | 0.73357 | $+1.1 \times 10^{-3}$ | −13 |
| $T_{surf}$ = 16° C. | 0.73272 | $+2.4 \times 10^{-4}$ | −3 |
| R = "Dry Grass" $H_2O$ = 50% RH | 0.71821 | $-1.4 \times 10^{-2}$ | +165 |

TABLE 5

Parametric analysis of errors in hypothetical retrieval of $C_2H_6$ using
multi-spectral data to retrieve surface reflectivity.

| Parameter Varied | "Measured" $S_{diff}/S_{avg}$ | Nominal $S_{diff}/S_{avg}$ | $\Delta(S_{diff}/S_{avg})$ | Error (ppm-m $C_2H_6$) |
|---|---|---|---|---|
| $C_2H_6$ = 10 ppm-m | 0.73239 | 0.73248 | $8.6 \times 10^{-4}$ | +10 |
| R = 10% | 0.73028 | 0.73028 | 0 | 0 |
| R = 'Asphalt Singles' | 0.73104 | 0.73092 | $1.2 \times 10^{-4}$ | −1.3 |
| R = "Dry Grass" | 0.71651 | 0.71632 | $1.9 \times 10^{-4}$ | −2.1 |
| R = "Ice" | 0.72307 | 0.72302 | $5 \times 10^{-5}$ | −0.6 |
| R = "Sandy Loam" | 0.7346 | 0.73492 | $-3.2 \times 10^{-4}$ | +3.6 |
| R = "Water" | 0.73109 | 0.73102 | $7 \times 10^{-5}$ | −0.8 |
| $CH_4$ = 1.8 ppm | 0.73237 | 0.7324 | $-3 \times 10^{-5}$ | +0.3 |
| $H_2O$ = 50% RH | 0.73357 | 0.73385 | $-2.8 \times 10^{-4}$ | +3.1 |
| $T_{surf}$ = 16° C. | 0.73272 | 0.73258 | $1.4 \times 10^{-4}$ | −1.6 |
| R = "Dry Grass" $H_2O$ = 50% RH | 0.71821 | 0.71823 | $-2 \times 10^{-5}$ | +0.2 |

TABLE 6

Description of Parameters and Defaults Used in Radiance Calculations.

| | | |
|---|---|---|
| Sun: | Temperature: | 5780 K |
| | Emission: | blackbody |
| | Solar Zenith Angle (SZA): | default: 0° |
| Atmosphere: | Max Altitude: | 50 km (0.0755 kPa) |
| | Dowelling Layers: | 25 (equal pressure layers) |
| | ZTP Profile: | US Standard (spring mid-latitudes) |
| | Upwelling Layers: | 1 (0 to 300 m) |
| | $H_2O$ Profile: | constant % RH troposphere, 40 ppm Stratosphere (default: 40% RH) |
| | $CH_4$ Profile: | default: 1.7 ppmv constant |
| Surface: | Reflectivity: | default: 5% diffuse |
| | Emissivity: | 1 − reflectivity (default: 95%) |
| | Temperature: | default: 288.15 K (15° C.) |
| Hyperspectrometer: | Spectral Resolution: | default: 20 cm$^{-1}$ |
| | Separation between Channels: | default: 20 cm$^{-1}$ |
| | Channel Response Profile: | boxcar (100%) or Triangular |

The embodiments of the invention in which an exclusive property or privilege is claimed are defined as follows:

1. A method of detecting a target gas, comprising the steps of:
traversing a target area with a gas-filter correlation radiometer having a field of view oriented towards the target area, the gas-filter correlation radiometer receiving reflected radiation in a passband from the target area and producing gas-filter correlation radiometer signals from the received reflected radiation;
determining a surface reflectivity spectral profile of the target area in at least the passband; and
determining the presence of the target gas in the target area based upon the received reflected radiation and the surface reflectivity spectral profile of the target area.

2. The method of claim 1 in which the step of determining the surface reflectivity spectral profile of the target area in at least the passband comprises obtaining multi-spectral measurements in at least the passband from the field of view of the gas-filter correlation radiometer.

3. The method of claim 2 in which the step of determining the surface reflectivity spectral profile of the target area in at least the passband comprises relating the multi-spectral measurements to signals generated by an atmospheric radiative transfer model.

4. The method of claim 3 in which the step of determining the surface reflectivity spectral profile of the target area in at least the passband comprises modifying a calibrated multi-spectral measurement using the signals generated by the atmospheric radiative transfer model.

5. The method of claim 3 in which the step of determining the surface reflectivity spectral profile of the target area in at least the passband comprises removing effects of thermal emission in the reflected radiation received from the target area.

6. The method of claim 5 in which removing effects of thermal emission comprises subtracting thermal emission effects from the multi-spectral measurements and the signals generated by the atmospheric radiative transfer model.

7. The method of claim 2 in which determining the presence of the target gas comprises comparing the gas-filter correlation radiometer signals with hypothetical gas-filter correlation radiometer signals.

8. The method of claim 7 further comprising generating the hypothetical gas-filter correlation radiometer signals by using an atmospheric radiative transfer model.

9. The method of claim 2 in which the gas-filter correlation radiometer signals and the multi-spectral measurements are respectively obtained using the gas-filter correlation radiometer and a separate spectrometer oriented to receive reflected radiation from the target area simultaneously.

10. The method of claim 2 in which the multi-spectral measurements are obtained by splitting the received reflected radiation into at least two separate paths within the gas-filter correlation radiometer, one of which paths is used to calculate the gas-filter correlation radiometer signals and the or another of which paths is used to calculate the multi-spectral measurements.

11. The method of claim 1 in which the step of determining the surface reflectivity spectral profile of the target area in at least the passband comprises relating the multi-spectral measurements to calibration measurements of surfaces of known reflectivity.

12. The method of claim 1 in which determining the presence of the target gas comprises comparing the gas-filter correlation radiometer signals with hypothetical gas-filter correlation radiometer signals.

13. The method of claim 12 further comprising generating the hypothetical gas-filter correlation radiometer signals by using an atmospheric radiative transfer model.

14. The method of claim 1 in which determining the presence of the target gas comprises determining a concentration of the target gas.

15. The method of claim 1 in which the gas-filter correlation radiometer has a passband that includes radiation in the range 3.25 to 3.51 µm.

16. The method of claim 1 in which the gas-filter correlation radiometer has a passband that includes significant thermal emission and reflected solar radiation.

17. A method of detecting a target gas, comprising the steps of:
measuring reflected radiation from the target area using a spectrometer;
determining a surface reflectivity spectral profile of a target area using the reflected radiation measured by the spectrometer and one or both of an atmospheric radiative transfer model and calibration measurements of surface reflectivity;
measuring reflected radiation from the target area using a gas-filter correlation radiometer; and
determining the presence of a target gas based on the reflected radiation measured by the gas-filter correlation radiometer and the surface reflectivity spectral profile.

18. A detector for detecting gases, comprising:
a gas-filter correlation radiometer having a first field of view oriented toward a target area;
the gas-filter correlation radiometer in operation having as input reflected radiation from the target area and having as radiometer output a first signal corresponding to detection of a target gas between the gas-filter correlation radiometer and the target area;
a spectrometer having a second field of view oriented toward the target area;
the spectrometer in operation having as input reflected radiation from the target area and having as spectrometer output a second signal corresponding to a surface reflectivity spectral profile of the target area; and
detector electronics connected to receive the radiometer output and the spectrometer output, the electronics having in operation as detector output a gas detection signal based on the radiometer output and the spectrometer output.

19. The detector of claim 18 in which the spectrometer and the gas-filter correlation radiometer are separate devices.

20. The detector of claim 18 in which the spectrometer has a spectrometer passband divided into channels, the gas-filter correlation radiometer has a radiometer passband and the channels of the spectrometer at least partially overlap with the radiometer passband.

21. The detector of claim 18 in which the gas-filter correlation radiometer and the spectrometer are contained within a single apparatus.

22. The detector of claim 21 in which the gas-filter correlation radiometer and the spectrometer share at least one converter of light to electrical energy.

23. The detector of claim 18 in which the spectrometer is an imaging spectrometer.

24. The detector of claim 18 in which the spectrometer comprises a detector array having a spatial dimension and a spectral dimension.

25. The detector of claim 18 in which the gas-filter correlation radiometer has a passband that includes radiation in the range 3.25 to 3.51 µm.

26. The detector of claim 18 in which the gas-filter correlation radiometer has a passband that includes significant thermal emission and reflected solar radiation.

* * * * *

UNITED STATES PATENT AND TRADEMARK OFFICE
CERTIFICATE OF CORRECTION

| | | |
|---|---|---|
| PATENT NO. | : 8,158,944 B2 | Page 1 of 1 |
| APPLICATION NO. | : 12/552248 | |
| DATED | : April 17, 2012 | |
| INVENTOR(S) | : B. T. Tolton et al. | |

It is certified that error appears in the above-identified patent and that said Letters Patent is hereby corrected as shown below:

In the Claims,

| COLUMN | LINE | ERROR |
|---|---|---|
| 17 | 53 | "and the or another of which" should read |
| (Claim 10, | line 5) | --and another of which-- |

Signed and Sealed this
Twenty-first Day of April, 2015

Michelle K. Lee
*Director of the United States Patent and Trademark Office*